US012773156B2

(12) United States Patent
Albert et al.

(10) Patent No.: US 12,773,156 B2
(45) Date of Patent: Oct. 27, 2026

(54) TWELVE-LEAD ELECTROCARDIOGRAM USING A REDUCED FORM-FACTOR MULTI-ELECTRODE DEVICE

(71) Applicant: AliveCor, Inc., Mountain View, CA (US)

(72) Inventors: David E. Albert, Oklahoma City, OK (US); Bruce Satchwell, Queensland (AU); Kim Norman Barnett, Brisbane (AU); Joel Q. Xue, Wauwatosa, WI (US)

(73) Assignee: AliveCor, Inc., Mountain View, CA (US)

( * ) Notice: Subject to any disclaimer, the term of this patent is extended or adjusted under 35 U.S.C. 154(b) by 225 days.

(21) Appl. No.: 17/465,714

(22) Filed: Sep. 2, 2021

(65) Prior Publication Data

US 2022/0304613 A1 Sep. 29, 2022

Related U.S. Application Data

(60) Provisional application No. 63/165,534, filed on Mar. 24, 2021.

(51) Int. Cl.
*A61B 5/364* (2021.01)
*A61B 5/00* (2006.01)
(Continued)

(52) U.S. Cl.
CPC ............ *A61B 5/364* (2021.01); *A61B 5/0006* (2013.01); *A61B 5/257* (2021.01); *A61B 5/271* (2021.01);
(Continued)

(58) Field of Classification Search
CPC ....... A61B 5/364; A61B 5/0006; A61B 5/257; A61B 5/271; A61B 5/282; A61B 5/308;
(Continued)

(56) References Cited

U.S. PATENT DOCUMENTS 4,850,370 A 7/1989 Dower
2011/0105928 A1 5/2011 Bojovic et al.
(Continued)

FOREIGN PATENT DOCUMENTS

WO WO-2015035251 A1 * 3/2015 ........... A61B 5/0006

OTHER PUBLICATIONS

Pearce, Arron, "Examining the causes and effects of electrode misplacement during electrocardiography: a literature review," British Journal of Cardiac Nursing, 2019, vol. 14, Issue No. 7, MA Healthcare Ltd, https://doi.org/10.12968/bjca.2019.0010.
(Continued)

*Primary Examiner* — Benjamin J Klein
*Assistant Examiner* — Daniel Tehrani
(74) *Attorney, Agent, or Firm* — Womble Bond Dickinson (US) LLP

(57) ABSTRACT

Embodiments of the present disclosure provide a small form factor ECG monitoring device that can acquire 3 standard ECG leads including a V-lead, does not require the use of adhesives for electrodes, and provides ECG data for a user on a near instantaneous basis. The ECG monitoring device can acquire leads I, II, and V2 (or any other V lead). The addition of a V-lead not only provides an additional channel of ECG data, but also adds another orthogonal cardiac field plane (the horizontal plane) thanks to the reference point formed by leads I and II. The ECG monitoring device may derive the augmented limb leads and subsequently generate a full 12-lead ECG. The ECG monitoring device may generate one or more diagnoses based on the full 12-lead set. The ECG monitoring device may provide an easy and non-invasive way for a person to take an ECG on the fly.

19 Claims, 19 Drawing Sheets

(51) Int. Cl.
*A61B 5/257* (2021.01)
*A61B 5/271* (2021.01)
*A61B 5/282* (2021.01)
*A61B 5/308* (2021.01)
*A61B 5/339* (2021.01)

(52) U.S. Cl.
CPC .............. *A61B 5/282* (2021.01); *A61B 5/308* (2021.01); *A61B 5/339* (2021.01); *A61B 2560/0475* (2013.01)

(58) Field of Classification Search
CPC ......... A61B 5/339; A61B 5/327; A61B 5/318; A61B 5/346; A61B 5/347; A61B 5/366; A61B 5/4836; A61B 5/24; A61B 2018/00839; A61B 5/349; A61B 5/6833; A61B 2018/00351; A61B 5/395; A61B 5/05; A61B 5/332; A61B 5/02438; A61B 5/02405; A61B 5/341; A61B 5/7278
See application file for complete search history.

(56) References Cited

U.S. PATENT DOCUMENTS

| | | | | |
|---|---|---|---|---|
| 2014/0228665 A1* | 8/2014 | Albert | .................. | A61B 5/0245 600/384 |
| 2017/0188861 A1* | 7/2017 | Schreck | ................. | A61B 5/327 |
| 2021/0219902 A1* | 7/2021 | Vajdic | .................... | G16H 50/20 |
| 2024/0197229 A1* | 6/2024 | Kranz | .................... | A61B 5/349 |

OTHER PUBLICATIONS

Kasha, John, "PhysioSign AL-EKG/ECG," Pitch Slides presentation, PhysioSign Inc., USA.
Martinez, Juan Pablo et al., "Assessment of QT-measurement accuracy using the 12-lead electrocardiogram derived from EASI leads," Journal of Electrocardiology, 2007, pp. 172-179, vol. 40, Elsevier Inc.
Martinez, Juan Pablo et al., "Accuracy of QT Measurement in the EASI-derived 12-lead ECG," Proceedings of the 28th IEEE EMBS Annual International Conference, 2006, pp. 3986-3989, New York, USA, https://www. researchgate.net/publication/5898233.
Ribeiro, Antonio H. et al., "Automatic diagnosis of the 12-lead ECG using a deep neural network," Nature Communications, 2020, vol. 11, https://doi.org/10.1038/s41467-020-15432-4.
Sohn, Jangjay et al., "Reconstruction of 12-Lead Electrocardiogram from a Three-Lead Patch-Type Device Using a LSTM Network," Sensors Journal, 2020, vol. 20, No. 11, https://doi.org/10.3390/s20113278.
Strodthoff, Nils et al., "Detecting and interpreting myocardial infarctions using fully convolutional neural networks," Physiological Measurement, 2018, vol. 40, No. 1, Institute of Physics and Engineering in Medicine.
Stark, Konstantin et al., "Watch out for ST-elevationmyocardial infarction: a case report of ST-elevation in single-lead electrocardiogram tracing of a smartwatch," Case reports, European Heart Journal, 2020, European Society of Cardiology, Oxford University Press.
Miller, Todd D. et al., "How many electrocardiogramads are required for exercise treadmill tests?" Journal of Electrocardiology, 1987, pp. 131-137, vol. 20, Issue No. 2, Elsevier Inc., https://doi.org/10.1016/S0022-0763(87) 80102-4.
Pandey, Bhasker et al., "Sudden Cardiac Death Risk Estimation Algorithms; A Review," Journal of Engineering, Mar. 2018, pp. 18-22, vol. 8, Issue No. 3, International organization of Scientific Research.
Buzby, Scott, "Time between STEMI symptom onset, procedure appears to be crucial in PCI outcomes," Cardiology Today, 2021, https://www.healio.com/news/cardiac-vascular-intervention/20210114/time-between-stemi-symptom-onset-procedure-appears-to-be-crucial-in-pci-outcomes?utm_source=selligent&utm_medium=email.
Vik, Jari, "Diagnostic Properties of Exercise Electrocardiogramads and Variables in the Detection of Coronary Artery Disease," Doctoral thesis, Doctor of Technology, Tempere University, Oct. 2000, Tempere, Finland.
Scherer, Julie A. et al., "Synthesis of the 12 Lead Electrocardiogram from a 3 Lead Semi-Orthogonal Subset Using Patient-Specific Linear Transformation Arrays," 1989, Department of Internal Medicine, Electrical Engineering and Computer Science, University of Michigan, Ann Arbor, Michigan.
Scherer, Julie A. et al., "Evaluation of 12-Lead ECG Synthesis Using Analysis Measurements in 240 Patients," 1992.
Atoui, H. et al., "A Neural Network Approach for Patient-Specific 12-lead ECG Synthesis in Patient Monitoring Environments," Computers in Cardiology, 2004, vol. 31, INSERM ERM107 Methodologies of Information Processing in Cardiology, Lyon, France.
Rubel, Paul et al., "Toward personal eHealth in cardiology. Results from the EPI-MEDICS telemedicine project," Journal of Electrocardiology, Jun. 10, 2005, vol. 38, Elsevier Inc.
Atoui, H. et al., "A Novel Neural-Network Model for Deeriving Standard 12-lead ECGs From Serial Three-Lead ECGs: Application to Self-Care," IEEE Transactions on Information Technology in Biomedicine, May 2010, vol. 14, No. 3, Lyon, France.
Schreck, David M. et al., "Derivation of the 12-lead electrocardiogram and 3-lead vectorcardiogram," American Journal of Emergency Medicine, Apr. 2013, vol. 31.
Maheshwari, S. et al., "Accurate and reliable 3-lead to 12-lead ECG reconstruction methodology for remote health monitoring applications," IRBM, 2014, vol. 35.
Chen, Fengjian et al., "Standard 12-lead ECG Synthesis Using a GA Optimized BP Neural Network," 7th International Conference on Advanced Computational Intelligence, Mar. 2015, Mount Wuyi, Fujian, China.
Zhu, Huaiyu et al., "A lightweight piecewise linear synthesis method for standard 12-lead ECG signals based on adaptive region segmentation," PLOS One, Oct. 19, 2018, vol. 13, No. 10.
Schreck, David M. et al., "Statistical Modeling: VI. Mathematical Modeling of the Electrocardiogram Using Factor Analysis," Academic Emergency Medicine, Sep. 1998, vol. 5, No. 9.
Dower et al., "Deriving the 12-lead Electrocardiogram From Four (EASI) Electrodes," Journal of Electrocardiology, 1988, S1182-S187.
Muhlestein, Joseph Boone et al., "Feasibility of combining serial smartphone single-lead electrocardiograms for the diagnosis of ST-elevation myocardial infarction," American Heart Journal, 2019, pp. 125-135, vol. 221, No. 0, Elsevier Inc.
Drew, Barbara J. et al., "Accuracy of the EASI 12-Lead Electrocardiogram Compared to the Standard 12-Lead Electrocardiogram for Diagnosing Multiple Cardiac Abnormalities," Journal of Electrocardiology, 1999, , vol. 32, Churchill Livingstone.
Lindow, Thomas et al., "Smartphone 12-lead ECG—Exciting but must be handled with care," Letters to the Editor, American Heart Journal, 2020.
Wehr, Gabriele et al., "A vector-based, 5-electrode, 12-lead monitoring ECG (EASI) is equivalent to conventional 12-lead ECG for diagnosis of acute coronary syndromes," Journal of Electrocardiology, 2006, pp. 22-28, vol. 39, Elsevier Inc.
Nelwan, Stefan P. et al., "Simultaneous comparison of 3 derived 12-lead electrocardiograms with standard electrocardiogram at rest and during percutaneous coronary occlusion," Journal of Electrocardiology, 2008, pp. 230-237, vol. 41, Elsevier Inc.
Mercer, B. et al., "A simple adaptation of a handheld ECG recorder to obtain chest lead equivalents," Journal Pre-proof, Journal of Electrocardiology, 2020, S0022-0736(20)30573-2, Elsevier, Inc., https://doi.org/10.1016/j.electrocard.2020.10.005.
Yang, Ting et al., "Big data reveals insights for lead importance in ECG interpretation," Journal Pre-proof, Journal of Electrocardiology, 2021, S0022-0736(21)00004-2, Elsevier Inc., https://doi.org/10.1016/j.jelectrocard.2021.01.002.
Zhao, Yifan et al., "Early detection of ST-segment elevated myocardial infarction by artificial intelligence with 12-lead electrocar-

(56) References Cited

OTHER PUBLICATIONS diogram," International Journal of Cardiology, 2020, pp. 223-230, vol. 317, Elsevier Inc., https://doi.org/10.1016/j.ijcard.2020.04.089.
Rokos, Ivan C., "Artificial intelligence for STEMI detection: The 'Shanghai Algorithm' provides a step forward," International Journal of Cardiology, 2020, pp. 231-232, vol. 317, Elsevier Inc., https://doi.org/10.1016/j.jcard.2020.07.002.
Mulyadi, Indra Hardian et al., "Improving accuracy of derived 12-lead electrocardiography by waveform segmentation," Indonesian Journal of Electrical Engineering and Informatics (IJEEI), Mar. 2019, pp. 15-21, vol. 7, No. 1, Institute of Advanced Engineering and Science.
Frisch, Stephanie O. et al., "Prevalence and Predictors of Delay in Seeking Emergency Care in Patients who Call 9-1-1 for Chest Pain," J Emerg Med., 2019, pp. 603-610, vol. 57, No. 5, HHS Public Access.
Nelwan, Stefan Paul, "Evaluation of 12-Lead Electrocardiogram Reconstruction Methods for Patient Monitoring,", Ph.D. Thesis, Nov. 2005, Optima Grafische Communicatie.
GE Healthcare, Marquette™ 12SL™, ECG Analysis Program, Physician's Guide 2056246-002C, 2019, GE Medical Systems Information Technologies, Inc., General Electric Company.
Tomasic, Ivan et al., "Electrocardiographic Systems With Reduced Numbers of Leads—Synthesis of the 12-Lead ECG," IEEE Reviews in Biomedical Engineering, 2014, vol. 7.
Trobec, Roman et al., "Synthesis of the 12-lead Electrocardiogram from Differential Leads," IEEE, 2011.
Lancia, Loreto et al., "Continuous ECG Monitoring in Patients With Acute Coronary Syndrome or Heart Failure: EASI Versus Gold Standard," Clinical Nursing Research, 2018, pp. 433-449, vol. 27, No. 4.
Coeytaux, Remy R., "Systematic Review of ECG-based Signal Analysis Technologies for Evaluating Patients With Acute Coronary Syndrome," Technology Assessment Report, Jun. 2012, Technology Assessment Program, Duke Evidence-based Practice Center.
Montavon, Berney et al., "Adaptive Filtering for Detecting Myocardial Infarction Using Noninvasive Conducting Polymer Composite Sensors," Proceedings of the LASRED International Symposia, Imaging and Signal Processing in Healthcare Technology, May 2012, Baltimore, USA.
Attia, Zachi I. et al., "Age and Sex Estimation Using Artificial Intelligence From Standard 12-Lead ECGs," Circulation: Arrhythmia and Electrophysiology, 2019, vol. 12, American Heart Association Inc., Wolters Kluwer Health, Inc.
Manocha, Amit Kumar et al., "An Overview of Ischemia Detection Techniques," International Journal of Scientific & Engineering Research, Nov. 2011, vol. 2, Issue No. 11, IJSER.
Smith, Stephen W. et al., "A deep neural network learning algorithm outperforms a conventional algorithm for emergency department electrocardiogram interpretation," Journal of Electrocardiology, 2019, pp. 88-95, vol. 52, Elsevier Inc.
CardioSecur, Scientific Background, Version 5.0.
Grant, Robert P., "Spatial Vector Electrocardiogramethod for Calculating the Spatial Electrical Vectors of the Heart from Conventional Leads," Circulation: Journal of the American Heart Association, 1950, pp. 676-695, vol. 2, No. 5, American Heart Association, Dallas, Texas, USA, http://circ.ahajournals.org/content/2/5/676.
Bhoi, Akash Humar, "Classification Probability Analysis for Arrhythmia and Ischemia Using Frequency Domain Features of QRS Complex," Int. J. Bio Automation, 2015, pp. 531-542, vol. 19. No. 4.
Khan, Gabriel M., "A new electrode placement method for obtaining 12-lead ECGs," Open Heart, 2015, vol. 2, No. 1, British Cardiovascular Society, http://dx.doi.org/10.1136/openhrt-2014-000226.
Oleksy, Wojciech et al., "Improved EASI ECG Model Obtained Using Various Machine Learning and Regression Techniques," IEEE, 2012, pp. 534-538.
Oleksy, Wojciech et al., "Improving EASI ECG Method Using Various Machine Learning and Regression Techniques to Obtain New EASI ECG Model," International Journal of Computer and Communication Engineering, Sep. 2012, pp. 287-289, vol. 1, No. 3.
Francis, Johnson, "ECG monitoring leads and special leads," Indian Pacing and Electrophysiology Journal, 2016, pp. 92-95, vol. 16, Issue No. 3, Indian Heart Rhythm Society, Elsevier Inc., http://dx.doi.org/10.1016/j.ipej.2016.07.003.
Tsouri, Gill R. et al., "Patient-Specific 12-Lead ECG Reconstruction From Sparse Electrodes Using Independent Component Analysis," IEEE Journal of Biomedical Health Informatics, Mar. 2014, pp. 476-482, vol. 18, No. 2.
Gusev, Marjan et al., "ECGalert: A Heart Attack Alerting System," Conference Paper, 2017, https://www.researchgate.net/publication/319577700.
Preetam, T.V.N. et al., "ECG Signal Analysis and Prediction of Heart Attack With the Help of Optimized Neural Network," Alochana Chakra Journal, Apr. 2020, pp. 497-506, vol. 9, Issue No. 4, Department of ECE, AVN Institute of Engineering and Technology, Hyderabad, India.
Drexler, Michael et al., "AppleWatch detecting coronary ischaemia during chest pain episodes or an apple a day may keep myocardial infarction away," Cardiovascular Flashlight, 2020, European Society of Cardiology, Oxford University Press.
Engel, Gregory et al., "Electrocardiogramrhythmia Risk Testing," Curr Probl Cardiol, Jul. 2004, pp. 365-432.
Lindow, Thomas et al., "Electrocardiographic changes in the differentiation of ischemic and non-ischemic ST elevation," Scandinavian Cardiovascular Journal, 2019, pp. 100-107, vol. 54, Issue No. 2, Informa UK Limited, https://doi.org/10.1080/14017431.2019.1705383.
Ivanovic, Marija D. et al., "Signal Quality in Reconstructed 12-Lead Ambulatory ECGs Recorded Using 3-Lead Device," IEEE, 2019, pp. 5481-5487.
Lancia, Loreto et al., "A comparison between EASI system 12-lead ECGs and standard 12-lead ECGs for improved clinical nursing practice," Journal of Clinical Nursing, 2006, pp. 370-377, Blackwell Publishing Ltd.
Jahrsdoerfer, Mary et al., "Clinical Usefulness of the EASI 12-Lead Continuous Electrocardiographic Monitoring System," Critical Care Nurse, Oct. 2005, pp. 28-38, vol. 25, No. 5, The American Association of Critical-Care Nurses, https://www.researchgate.net/publication/7580087.
Almeida, Rute et al., "Multilead ECG delineation using spatially projected leads from wavelet transform loops," IEEE Transactions on Biomedical Engineering, 2008.
Gregg, R.E. et al., "Limitations on the Re-Use of Patient Specific Coefficients for 12-Lead ECG Reconstruction," Computers in Cardiology, 2008, pp. 209-212, vol. 35, ISSN 0276-6574.

* cited by examiner

TWELVE-LEAD ELECTROCARDIOGRAM USING A REDUCED FORM-FACTOR MULTI-ELECTRODE DEVICE

CROSS-REFERENCE

The present application claims the benefit of U.S. Provisional Application No. 63/165,534, filed Mar. 24, 2021 and entitled "12 LEAD ELECTROCARDIOGRAM (ECG) DEVICE WITH REDUCED FORM FACTOR," the full contents of which are incorporated herein by reference.

TECHNICAL FIELD

The present disclosure relates to medical devices, systems, and methods and in particular, to small form-factor devices for providing electrocardiogram (ECG) monitoring.

BACKGROUND

Cardiovascular diseases are the leading cause of death in the world. In 2008, 30% of all global death can be attributed to cardiovascular diseases. It is also estimated that by 2030, over 23 million people will die from cardiovascular diseases annually. Cardiovascular diseases are prevalent across populations of first and third world countries alike, and affect people regardless of socioeconomic status.

Arrhythmia is a cardiac condition in which the electrical activity of the heart is irregular or is faster (tachycardia) or slower (bradycardia) than normal. Although many arrhythmias are not life-threatening, some can cause cardiac arrest and even sudden cardiac death. Indeed, cardiac arrhythmias are one of the most common causes of death when travelling to a hospital. Atrial fibrillation (A-fib) is the most common cardiac arrhythmia. In A-fib, electrical conduction through the ventricles of heart is irregular and disorganized. While A-fib may cause no symptoms, it is often associated with palpitations, shortness of breath, fainting, chest pain or congestive heart failure and also increases the risk of stroke. A-fib is usually diagnosed by taking an electrocardiogram (ECG) of a subject. To treat A-fib, a patient may take medications to slow heart rate or modify the rhythm of the heart. Patients may also take anticoagulants to prevent stroke or may even undergo surgical intervention including cardiac ablation to treat A-fib. In another example, an ECG may provide decision support for Acute Coronary Syndromes (ACS) by interpreting various rhythm and morphology conditions, including Myocardial Infarction (MI) and Ischemia.

Often, a patient with A-fib (or other type of arrhythmia) is monitored for extended periods of time to manage the disease. For example, a patient may be provided with a Holter monitor or other ambulatory electrocardiography device to continuously monitor the electrical activity of the cardiovascular system for e.g., at least 24 hours. Such monitoring can be critical in detecting conditions such as acute coronary syndrome (ACS), among others.

The American Heart Association and the European Society of Cardiology recommends that a 12-lead ECG should be acquired as early as possible for patients with possible ACS when symptoms present. Prehospital ECG has been found to significantly reduce time-to-treatment and shows better survival rates. The time-to-first-ECG is so vital that it is a quality and performance metric monitored by several regulatory bodies. According to the national health statistics for 2015, over 7 million people visited the emergency department (ED) in the United States (U.S.) with the primary complaint of chest pain or related symptoms of ACS. In the US, ED visits are increasing at a rate of or 3.2% annually and outside the U.S. ED visits are increasing at 3% to 7%, annually.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the invention are utilized, and the accompanying drawings of which:

DETAILED DESCRIPTION

It is to be understood that the present disclosure is not limited in its application to the details of construction, experiments, exemplary data, and/or the arrangement of the components set forth in the following description. The embodiments of the present disclosure are capable of other embodiments or of being practiced or carried out in various ways. Also, it is to be understood that the terminology employed herein is for purpose of description and should not be regarded as limiting.

In the following detailed description of embodiments of the present disclosure, numerous specific details are set forth in order to provide a more thorough understanding of the disclosure. However, it will be apparent to one of ordinary skill in the art that the concepts within the disclosure can be practiced without these specific details. In other instances, well-known features have not been described in detail to avoid unnecessarily complicating the description.

An electrocardiogram (ECG) provides a number of ECG waveforms that represent the electrical activity of a person's heart. An ECG monitoring device may comprise a set of electrodes for recording these ECG waveforms (also referred to herein as "taking an ECG") of the patient's heart. The set of electrodes may be placed on the skin of the patient in multiple locations and the electrical signal (ECG waveform) recorded between each electrode pair in the set of electrodes may be referred to as a lead. Varying numbers of leads can be used to take an ECG, and different numbers and combinations of electrodes can be used to form the various leads. Example numbers of leads used for taking ECGs are 1, 2, 6, and 12 leads.

The ECG waveforms (each one corresponding to a lead of the ECG) recorded by the ECG monitoring device may comprise data corresponding to the electrical activity of the person's heart. A typical heartbeat may include several variations of electrical potential, which may be classified into waves and complexes, including a P wave, a QRS complex, a T wave, and a U wave among others, as is known in the art. Stated differently, each ECG waveform may include a P wave, a QRS complex, a T wave, and a U wave among others, as is known in the art. The shape and duration of these waves may be related to various characteristics of the person's heart such as the size of the person's atrium (e.g., indicating atrial enlargement) and can be a first source of heartbeat characteristics unique to a person. The ECG waveforms may be analyzed (typically after standard filtering and "cleaning" of the signals) for various indicators that are useful in detecting cardiac events or status, such as cardiac arrhythmia detection and characterization. Such indicators may include ECG waveform amplitude and morphology (e.g., QRS complex amplitude and morphology), R wave-ST segment and T wave amplitude analysis, and heart rate variability (HRV), for example.

Figure 1A:
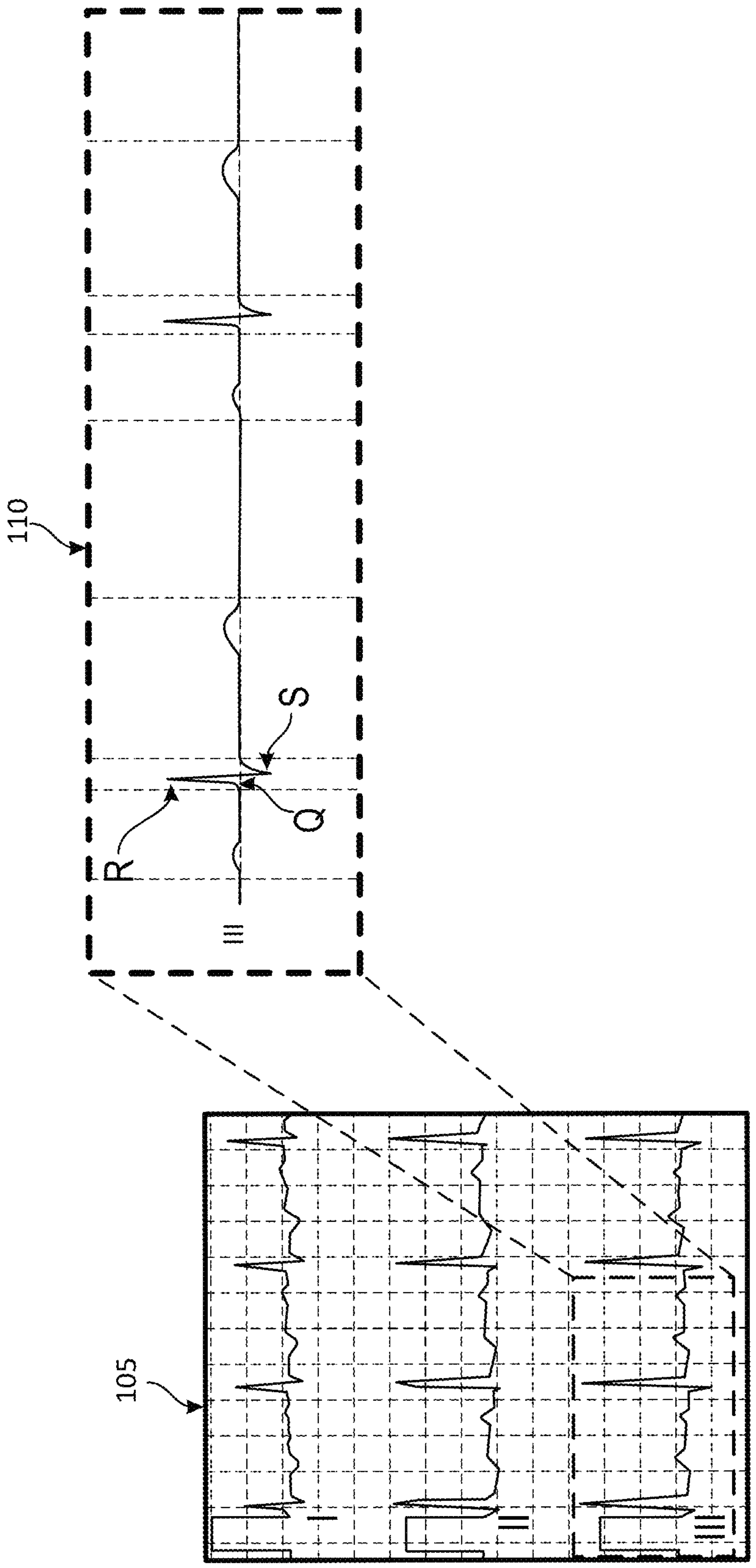
FIG. 1A is a diagram illustrating electrocardiogram (ECG) waveforms, in accordance with some embodiments of the present disclosure.

As noted above, ECG waveforms are generated from measuring multiple leads (each lead formed by a different electrode pair), and the ECG waveform obtained from each different electrode pair/lead may be different/unique (e.g., may have different morphologies/amplitudes). This is because although the various leads may analyze the same electrical events, each one may do so from a different angle. FIG. 1A illustrates a view 105 of an ECG waveform detected by each of 3 leads (I, II, and III) when a 3-lead ECG is taken as well as an exploded view 110 of the ECG waveform measured by lead III illustrating the QRS complex. As shown, the amplitudes and morphologies of the ECG waveform taken from leads I-III are all different, with the ECG waveform measured by lead III having the largest amplitude and the ECG waveform measured by lead I having the smallest amplitude.

There are different "standard" configurations for electrode placement that can be used to place electrodes on the patient. For example, an electrode placed on the right arm can be referred to as RA. The electrode placed on the left arm can be referred to as LA. The RA and LA electrodes may be placed at the same location on the left and right arms, preferably near the wrist in some embodiments. The leg electrodes can be referred to as RL for the right leg and LL for the left leg. The RL and LL electrodes may be placed on the same location for the left and right legs, preferably near the ankle in some embodiments. Lead I is typically the voltage between the left arm (LA) and right arm (RA), e.g. I=LA−RA. Lead II is typically the voltage between the left leg (LL) and right arm (RA), e.g. II=LL−RA. Lead III is the typically voltage between the left leg (LL) and left arm (LA), e.g. III=LL−LA. Augmented limb leads can also be determined from RA, RL, LL, and LA. The augmented vector right (aVR) lead is equal to RA−(LA+LL)/2 or −(I+II)/2. The augmented vector left (aVL) lead is equal to LA−(RA+LL)/2 or I−II/2. The augmented vector foot (aVF) lead is equal to LL−(RA+LA)/2 or II−I/2.

Figure 1B:
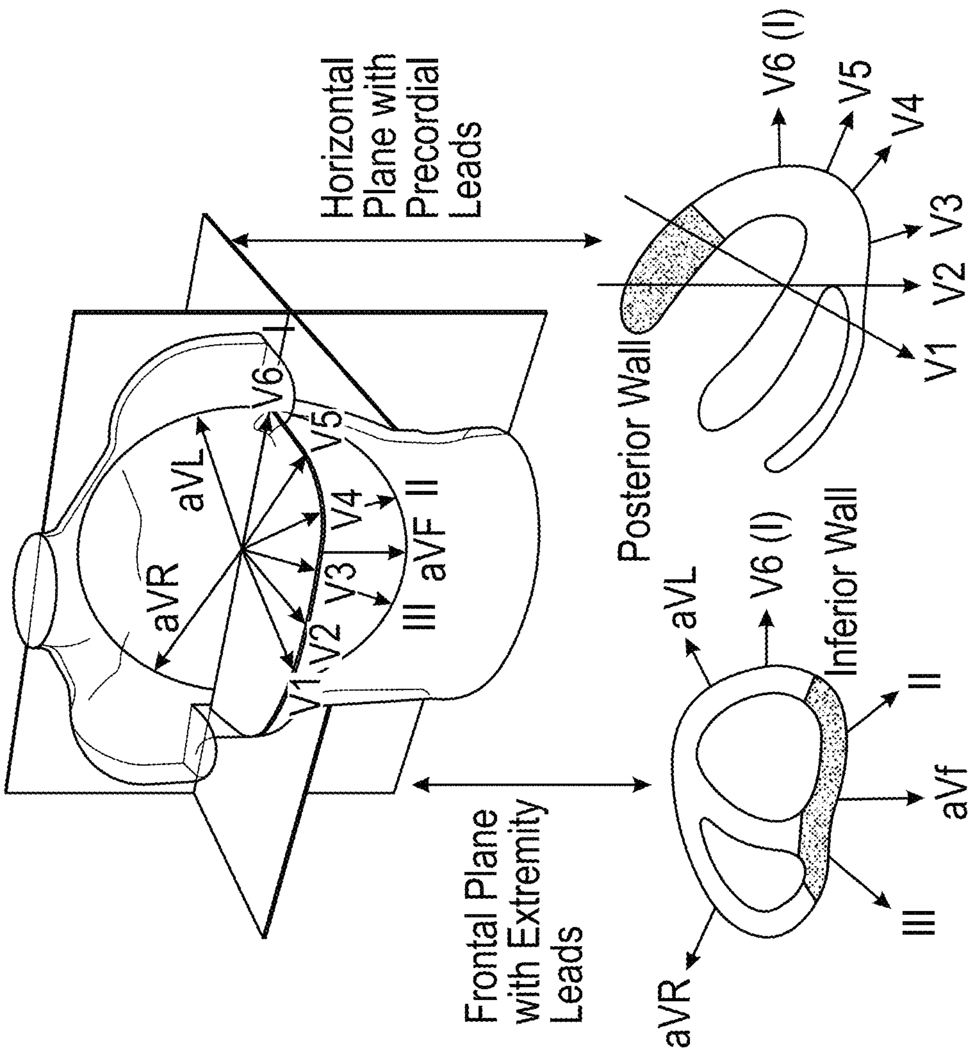
FIG. 1B illustrates a single dipole heart model with a 12 lead set represented on a hexaxial system, in accordance with some embodiments of the present disclosure.

FIG. 1B illustrates a single dipole heart model 115 with a 12 lead set comprising the I, II, III, aVR, aVL, aVF, V1, V2, V3, V4, V5, and V6 leads, all represented on a hexaxial system. The heart model 115 assumes a homogeneous cardiac field in all directions that only changes magnitude and direction with the cycle time. As illustrated in FIG. 1B, there are 2 orthogonal planes, the frontal plane and the horizontal plane. Inside each plane, there are several leads to cover the whole plane. In the frontal plane, there are 2 independent leads I and II, and 4 other derived leads III, aVR, aVL, and aVF, each 30 degrees apart. The reason the frontal plane has 2 independent leads is that they are far-field leads, each of which can cover a wider perspective but provide less detail, like a wide-angle camera lens. In the horizontal plane, there are normally 6 independent leads which are all closer to the heart than limb leads and may be referred to as near-field leads. Following the same analogy of a camera, the near-field leads may behave like a zoom-lens that covers less perspective, but with more accuracy towards local activity like ischemia and infarction. The two orthogonal planes are related by using a synthetic reference point formed by Leads I & II, called the Wilson-Central-Terminal (WCT). It is defined as RA+LA+RL/3 but given that both Lead I and II are recorded with reference to the RA so that the voltage of the RA can be considered zero, the WCT (VW) can be calculated using the RA as the reference for both Leads I & II (thus, assuming it to have zero potential) as:

Lead I+Lead II/3.

It should be noted that a set of two or more leads may be transformed to generate a full, 12-lead ECG. Such transformation may be performed using a machine learning model (e.g., a neural network, deep-learning techniques, etc.). The machine learning model may be trained using 12-lead ECG data corresponding to a population of individuals. The data, before being input into the machine learning model, may be pre-processed to filter the data in a manner suitable for the application. For example, data may be categorized according to height, gender, weight, nationality, etc. before being used to train one or more machine learning models, such that the resulting one or models are finely-tuned the specific types of individuals. In a further embodiment, the machine learning model may be further trained based on a user's own ECG data, to fine-tune and personalize the model even further to decrease any residual synthesis error.

As discussed herein, a 12-lead ECG should be acquired as early as possible for patients with possible ACS when symptoms present as prehospital ECG has been found to significantly reduce time-to-treatment and shows better survival rates. In addition, current ambulatory ECG devices such as Holter monitors, are typically bulky and difficult for subjects to administer without the aid of a medical professional. For example, the use of Holter monitors requires a patient to wear a bulky device on their chest and precisely place a plurality of electrode leads on precise locations on their chest. These requirements can impede the activities of the subject, including their natural movement such as bathing and showering. Once an ECG is taken by such devices, the ECG is sent to the subject's physician who then analyzes the ECG waveforms and provides a diagnosis and other recommendations. Currently, this process often must be performed through hospital administrators and health management organizations and many patients do not receive feedback in an expedient manner.

A number of handheld ECG measurement devices are known, including devices that may adapt existing mobile telecommunications device (e.g., smartphones) so that they can be used to record ECS. However, such devices either require the use of external (e.g., plug-in) electrodes, or include electrodes in a housing that are difficult to properly hold and apply to the body. Many ECG monitors are also limited to acquiring limb leads (e.g., due to size and other constraints). However, as people age, their QRS and T-wave vector may gradually move from the frontal plane to the horizontal plane, thus increasing the importance of acquiring data from a horizontal plane lead.

Embodiments of the present disclosure address the above and other problems by providing a small form factor ECG monitoring device that can acquire 3 standard ECG leads including a V-lead, does not require the use of adhesives for electrodes, can be used by a user/patient, and provides ECG data for a user on a near instantaneous basis. For example, the ECG monitoring device can acquire leads I, II, and V2 (or any other V lead). As discussed above, because leads I and II are both limb leads they are relatively far from the heart compared with the chest leads (V1-V6). The addition of a V-lead not only provides an additional channel of ECG data, but also adds another orthogonal cardiac field plane (the horizontal plane) thanks to the reference point formed by leads I and II. For example, the three electrode ECG monitoring device can be used to determine lead I (e.g., the voltage between the left arm and right arm) contemporaneously with lead II (e.g., the voltage between the left leg and right arm), and lead I contemporaneously with lead V2 or any other chest lead such as V5. However, any other combination of leads is possible. The ECG monitoring device may have a small form factor and may provide an easy and non-invasive way for a person to take an ECG on the fly. The ECG monitoring device may subsequently generate a 12-lead ECG using the three measured leads.

As discussed herein, for patients potentially suffering from ACS, including Myocardial Infarction (MI) and Ischemia, a 12 lead ECG should be taken as early as possible to reduce the time to diagnosis and the time to treatment. The ECG monitoring device in accordance with embodiments of the present disclosure may provide decision support to physicians for ACS from the home of a patient itself, and provides a convenient way for doctors to order 12-lead ECG tests and view reports as often as is necessary for them to manage the health of their patients, especially if they suspect ACS. In addition, an ECG monitoring device in accordance with embodiments of the present disclosure may prevent a patient from undergoing the inconvenience and disruption of an office visit and may save the cost and time of utilizing an ECG technician in the physician's office.

Figure 2A:
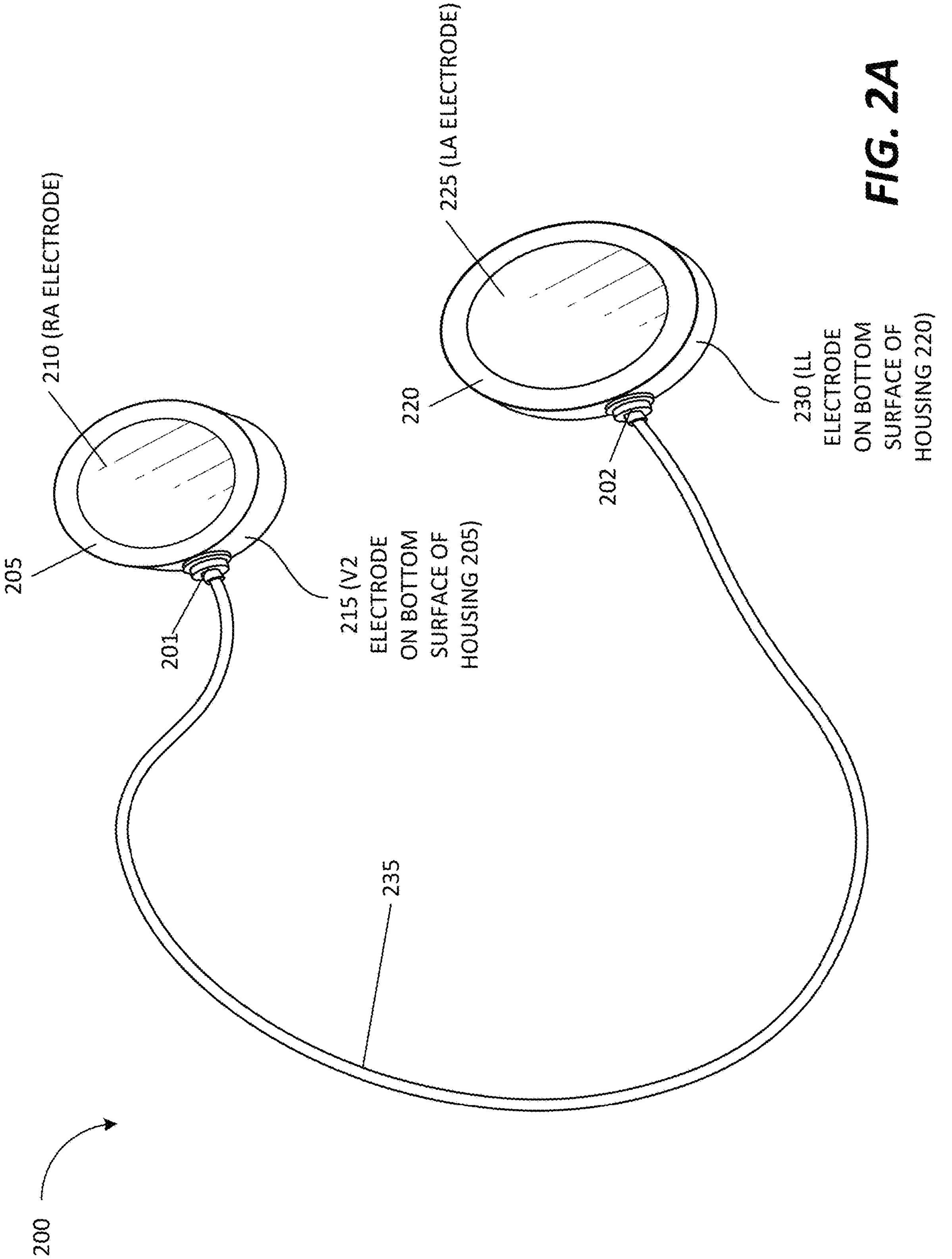
FIG. 2A is a diagram illustrating an ECG monitoring device, in accordance with some embodiments of the present disclosure.

FIG. 2A shows an ECG monitoring device 200 in accordance with some embodiments of the present disclosure. The ECG monitoring device 200 may comprise a first housing 205, and a second housing 220. An electrode 210 may be mounted on a top surface of the first housing 205 and an electrode 215 may be mounted on a bottom surface of the first housing 205. In the example of FIG. 2A, the electrode 210 may be a right arm (RA) electrode and the electrode 215 may be a V2 electrode. An electrode 225 may be mounted on a top surface of the second housing 220 and an electrode 230 may be mounted on a bottom surface of the second housing 220. In the example of FIG. 2A, the electrode 225 may be a left arm (LA) electrode and the electrode 230 may be a left leg (LL) electrode. As shown in FIG. 2A, each of the housing 205 and the housing 220 are in the shape of a circular puck, however each of the housing 205 and the housing 220 may be implemented or realized in any appropriate shape and using any appropriate material. Each of the electrodes of the ECG monitoring device 200 may be made of titanium nitride or any other appropriate material.

Each of the first and second housings 205 and 220 may include a connection socket 201 and 202 respectively. The first housing 205 may be coupled to the second housing 220 via cable 235 which may be plugged into the connection sockets 201 and 202 of housing 205 and housing 220 respectively and which may be any appropriate cable which can facilitate the transfer of data between housing 205 and housing 220 (using any appropriate data transfer protocol such as e.g., USB). For example, the cable 235 may be a USB cable and the connection socket of each of housing 205 and 220 may comprise a USB socket. Although illustrated as having only 1 connection socket, the embodiments of the present disclosure are not limited in this way and the housing 205 (as well as the housing 220 in some embodiments) may include any appropriate number of connection sockets to connect to one or more other housings or traditional stick on electrodes, as discussed in further detail herein. In other embodiments, the cable 235 may not be removable and may be permanently integrated to both housing 205 and 220.

Figure 2B:
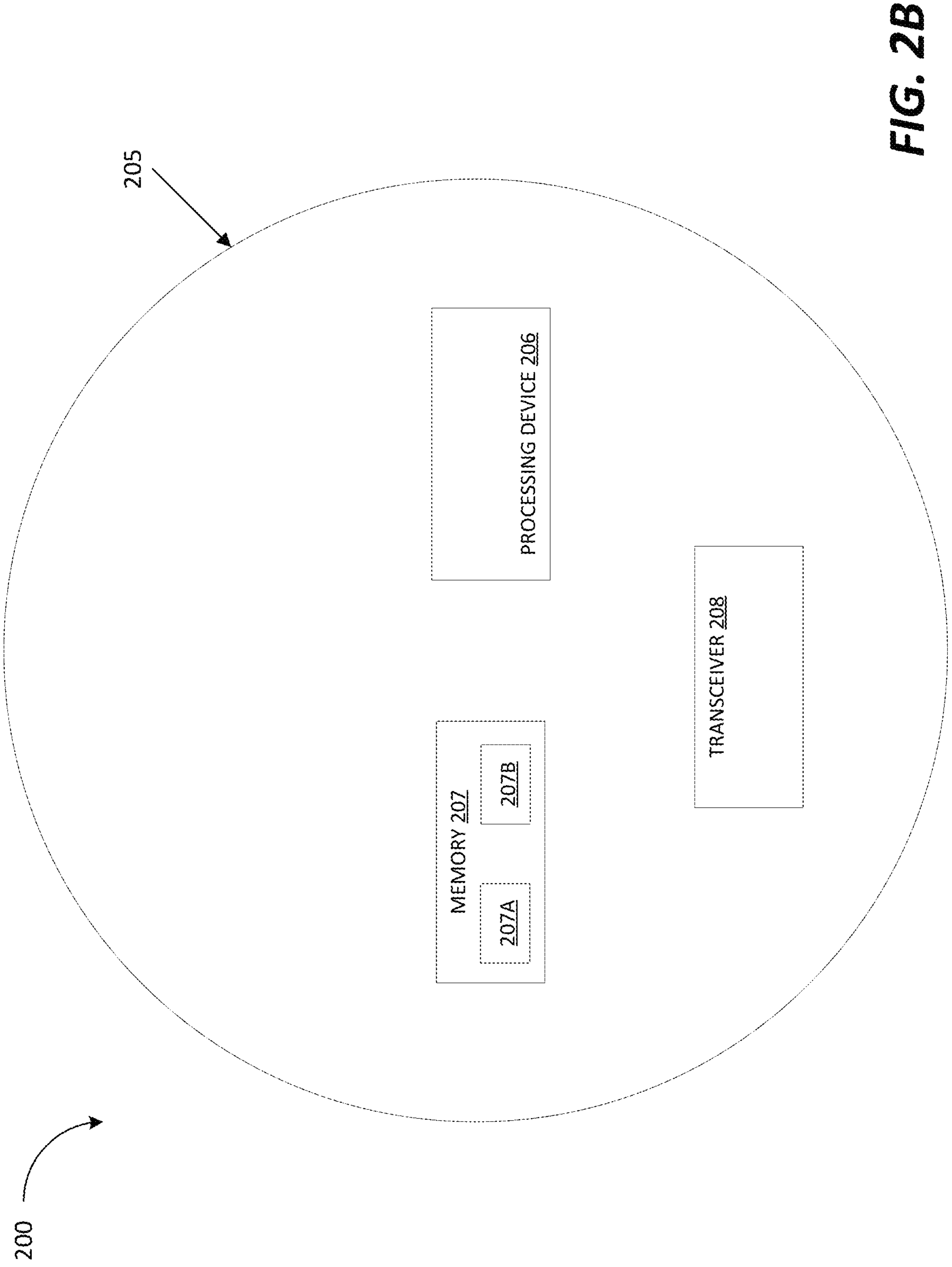
FIG. 2B is a hardware block diagram of the ECG monitoring device of FIG. 2A, in accordance with some embodiments of the present disclosure.

The housing 205 may comprise hardware to perform the functions described herein. FIG. 2B illustrates a hardware block diagram of housing 205 which may include hardware such as processing device 206 (e.g., processors, central processing units (CPUs)), memory 207 (e.g., random access memory (RAM), storage devices (e.g., hard-disk drive (HDD)), solid-state drives (SSD), etc.), and other hardware devices (e.g., analog to digital converter (ADC) etc.). A storage device may comprise a persistent storage that is capable of storing data. A persistent storage may be a local storage unit or a remote storage unit. Persistent storage may be a magnetic storage unit, optical storage unit, solid state storage unit, electronic storage units (main memory), or similar storage unit. Persistent storage may also be a monolithic/single device or a distributed set of devices. In some embodiments, the processing device 206 may comprise a dedicated ECG waveform processing and analysis chip that provides built-in leads off detection. The housing 205 may include an ADC (not shown) having a high enough sampling frequency for accurately converting the ECG waveforms measured by the set of electrodes into digital signals (e.g., a 24 bit ADC operating at 500 Hz or higher) for processing by the processing device 206.

The housing 205 may further comprise a transceiver 208, which may implement any appropriate protocol for transmitting ECG data wirelessly to one or more local and/or remote computing devices. For example, the transceiver 208 may comprise a Bluetooth™ chip for transmitting ECG data via Bluetooth to local computing devices (e.g., a laptop or smart phone of the user). In other embodiments, the transceiver 208 may include (or be coupled to) a network interface device configured to connect with a cellular data network (e.g., using GSM, GSM plus EDGE, CDMA, quadband, or other cellular protocols) or a WiFi (e.g., an 802.11 protocol) network, in order to transmit the ECG data to a remote computing device (e.g., a computing device of a physician or healthcare provider) and/or a local computing device. In some embodiments, both the housing 205 and the housing 220 may include the hardware described hereinabove (e.g., processing devices, memory, transceivers) and the functions described herein may be performed by either of housing 205 or housing 220.

The memory 207 may include a lead synthesis software module 207A (hereinafter referred to as module 207A) and an ECG waveform interpretation software module 207B (hereinafter referred to as module 207B). The processing device 205 may execute the module 207A to synthesize ECG waveforms corresponding to leads that were not measured by the electrodes of the ECG monitoring device 200 as discussed in further detail herein. The processing device 205 may execute the module 207B to generate diagnostic interpretations based on the measured and synthesized ECG waveforms, as discussed in further detail herein.

Figure 3A:
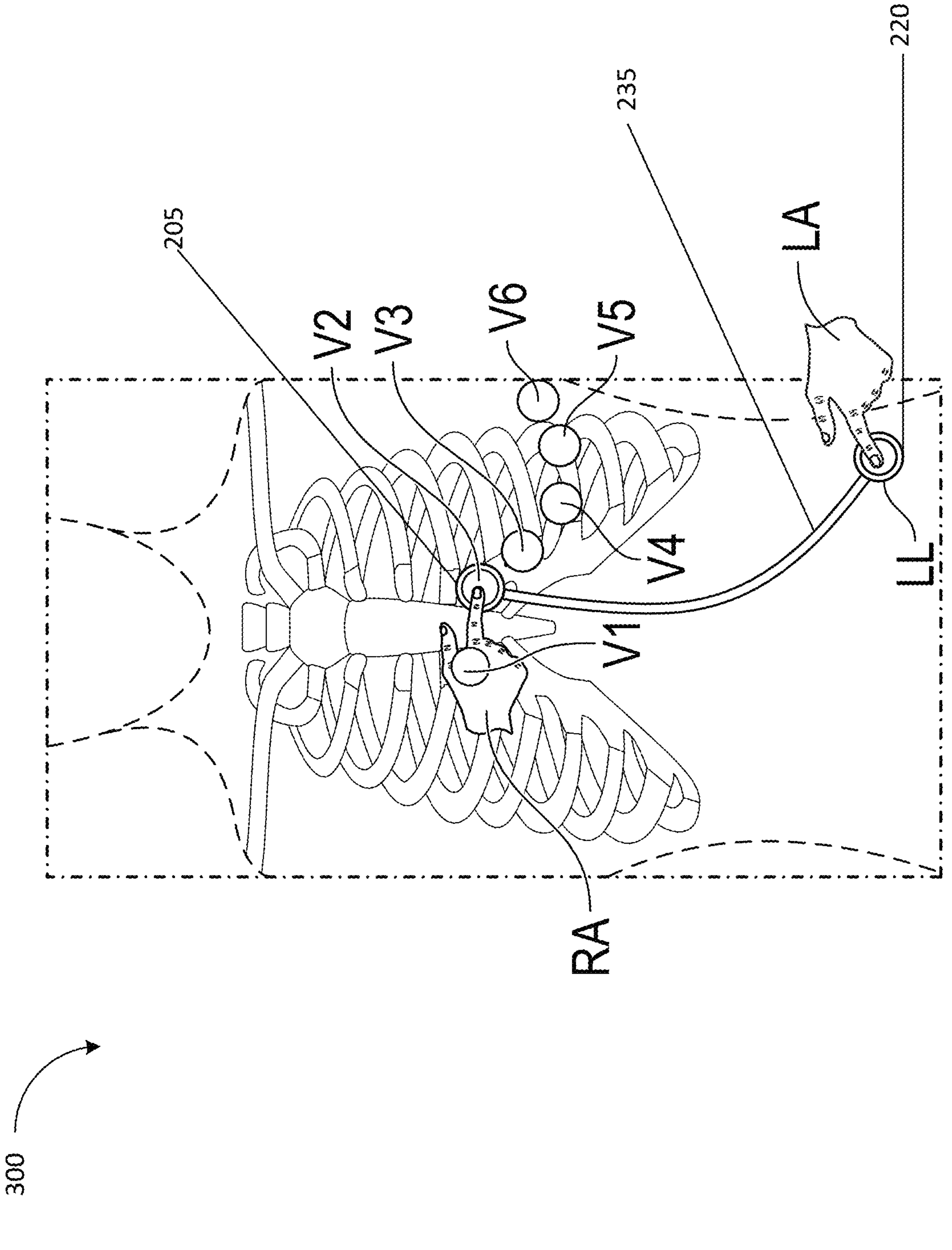
FIGS. 3A and 3B illustrate the ECG monitoring device of FIG. 2A in operation, in accordance with some embodiments of the present disclosure.
Figure 3B:
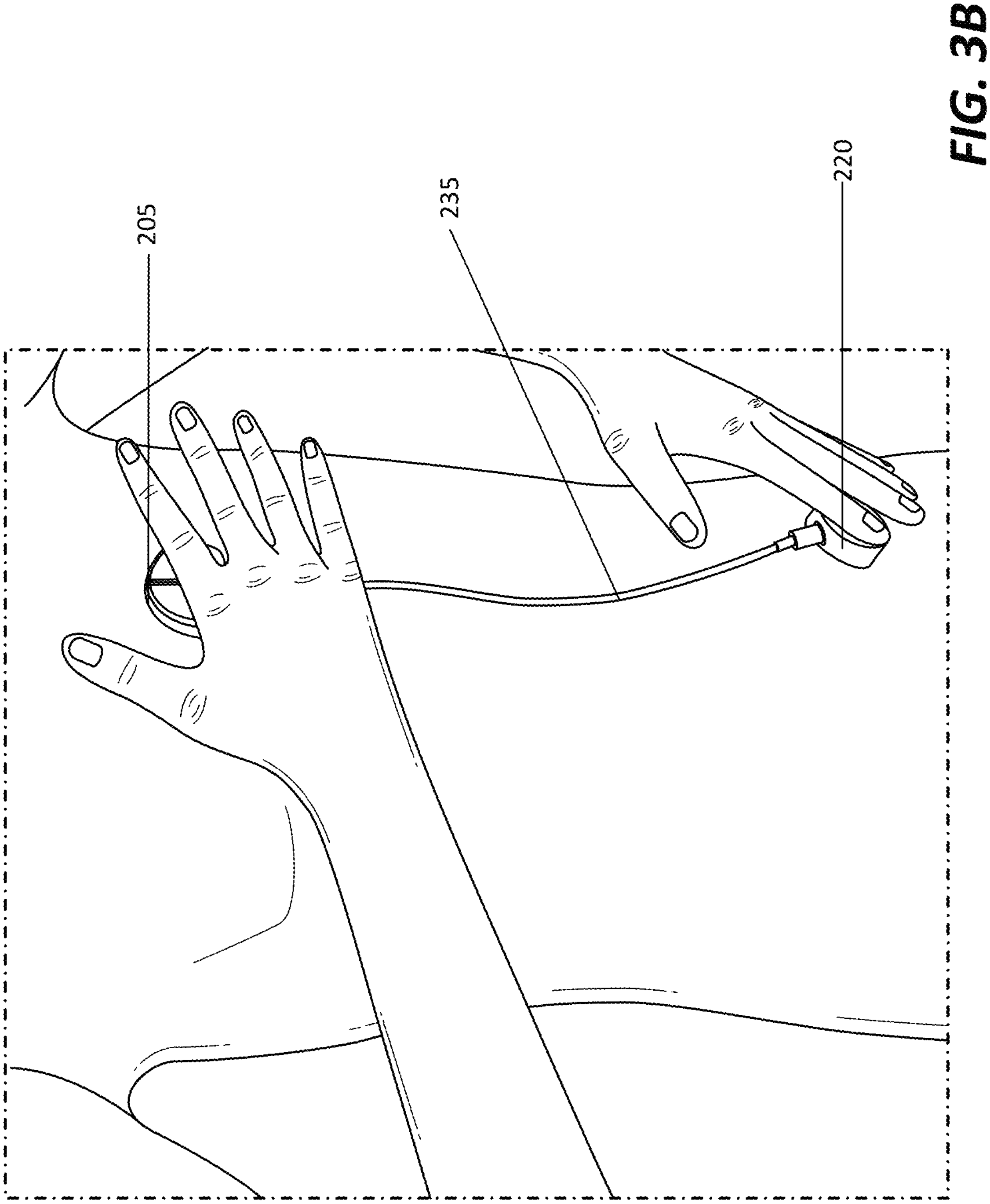

FIGS. 3A and 3B illustrate the ECG monitoring device 200 in operation. To take an ECG, the user may position each housing 205 and 220 of the ECG monitoring device 200 at the appropriate location as indicated in FIG. 3A. The user may position the two housings 205 and 220 such that electrodes 215 and 230 are in contact with the V2 and LL positions respectively, while touching electrodes 210 and 225 (the RA and LA electrodes respectively) on the top of each housing with their left and right hand respectively. More specifically, the user's right arm (right hand) may contact electrode 210 e.g., while simultaneously holding the housing 205 against the appropriate location on the user's chest such that electrode 215 (the V2 electrode) contacts the V2 location on the user's chest (see FIG. 3B). Similarly, the user's left arm (left hand) may contact electrode 225 e.g., while simultaneously holding the housing 220 against the user's left leg such that electrode 230 (LL electrode) contacts the left leg of the user (see FIG. 3B). This allows ECG monitoring device 200 to take a 3-lead ECG. More specifically, processing device 206 may utilize the electrodes of housing 205 and housing 220 to simultaneously record leads I, II, and V2 and subsequently derive leads III, aVR, aVL, aVF, as discussed hereinabove. Processing device 206 may then execute module 207A to synthesize the V1, V3, V4, V5, and V6 leads based on the I, II, III, aVR, aVL, aVF, and V2 leads using a lead conversion ML model (e.g., a state space model transform or neural network) to reconstruct a standard 12 lead ECG (as discussed in further detail herein).

The processing device 206 may then execute the module 207B in order to analyze the full 12 lead ECG waveform set and generate one or more interpretations (also referred to herein as diagnoses) based thereon using an interpretation ML model. The interpretation ML model may be based on any appropriate algorithm such as GE's EK12 algorithms. The processing device 206 may detect (and generate interpretations indicating) conditions such as myocardial ischemia (anterior or lateral ischemia), MI (anterior or lateral MI), left and right bundle branch block, and right/left ventricular hypertrophy, among others.

Figure 2C:
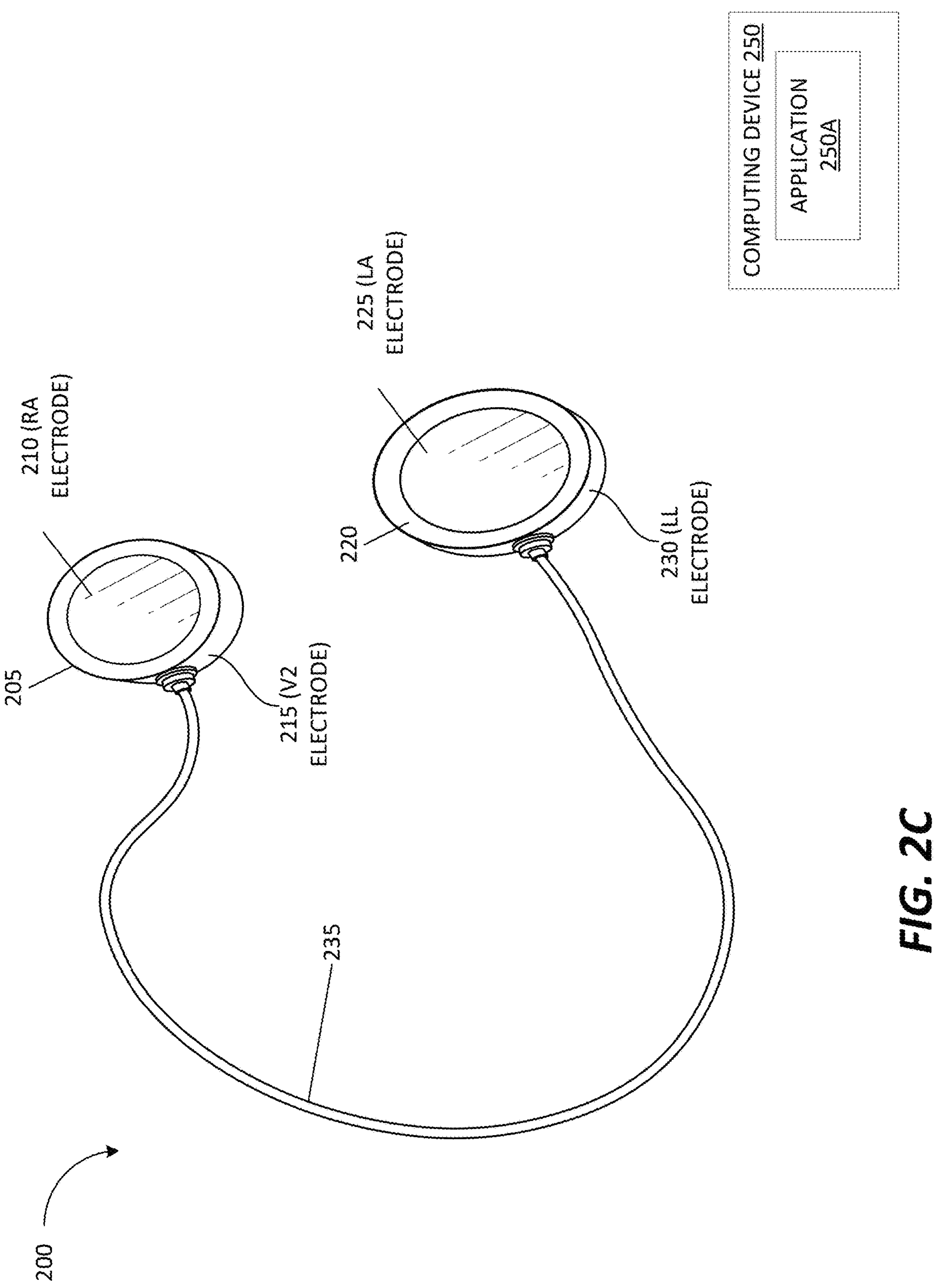
FIG. 2C is a diagram illustrating a computing device 250 for providing instructions for use of the ECG monitoring device of FIG. 2A, with some embodiments of the present disclosure.

Referring to FIG. 2C, in some embodiments, in order to ensure that the user places the electrodes of each housing 205 and 220 in the correct location, a computing device 250 of the user may provide instructions to the user for positioning the ECG monitoring device 200. In some embodiments, the computing device 250 may include an application 250A that provides a video to assist the user in finding the appropriate location for positioning each of the housing 205 and 220. For example, the video may instruct the user in finding the V2 location (4$^{th}$ intercostal space to the left of the sternum) where the electrode 210 should be placed. In other embodiments, the computing device 250 may include teleconferencing software (not shown) to allow the user to engage in a video chat or phone call with a nurse or ECG technician to help guide the user. In other embodiments, the user may share a picture of themselves via computing device 250 and a healthcare professional or automated (e.g., artificial intelligence-based system) can mark the appropriate location on the picture where the electrode should be placed. In some embodiments, if the user is not comfortable sharing pictures of themselves, the computing device 250 may include a virtual reality (VR) application (not shown) that generates a VR representation of the user on which the V2 and other relevant locations may be marked.

Figure 3C:
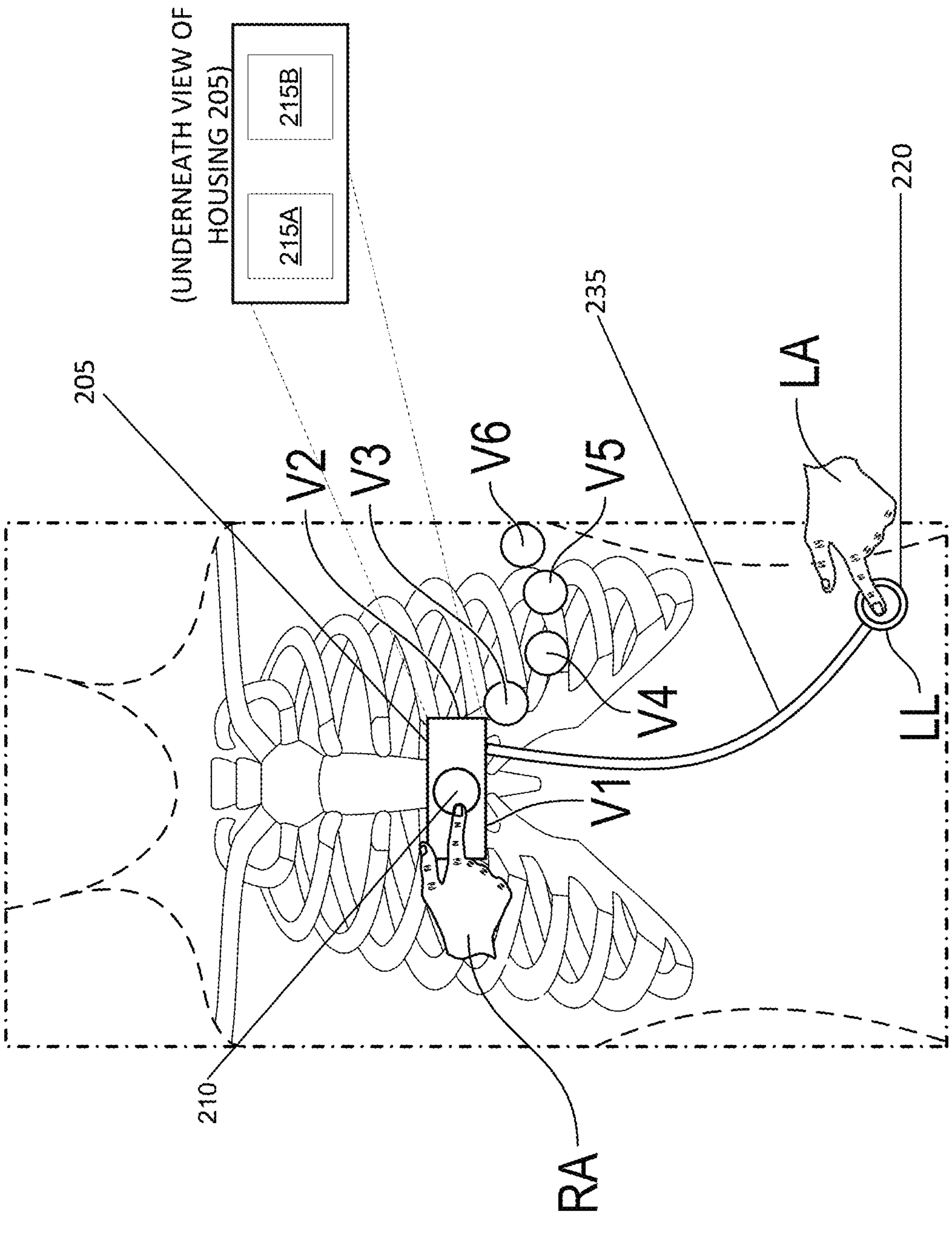
FIG. 3C illustrates the ECG monitoring device of FIG. 2A with a rectangular housing in operation, in accordance with some embodiments of the present disclosure.

FIG. 3C illustrates an embodiment in which the housing 205 may be rectangle shaped, so as to accommodate two electrodes 215A and 215B (shown as rectangle shaped in FIG. 3C but can be implemented in any appropriate shape) instead of a single electrode 215 as illustrated in FIGS. 2 and 3A. In the embodiment illustrated in FIG. 3C, the electrodes 215A and 215B may contact the V1 and V2 positions respectively, while the electrode 230 is in contact with the LL position, and electrodes 210 and 225 (the RA and LA electrodes respectively) on the top of each housing are contacting the left and right hand of the user respectively. In this manner, the device 200 may be used to take a four channel ECG. More specifically, processing device 206 may utilize the electrodes of housing 205 and housing 220 to simultaneously record leads I, II, V1, and V2, and subsequently derive leads III, aVR, aVL, aVF, as discussed hereinabove.

Figure 3D:
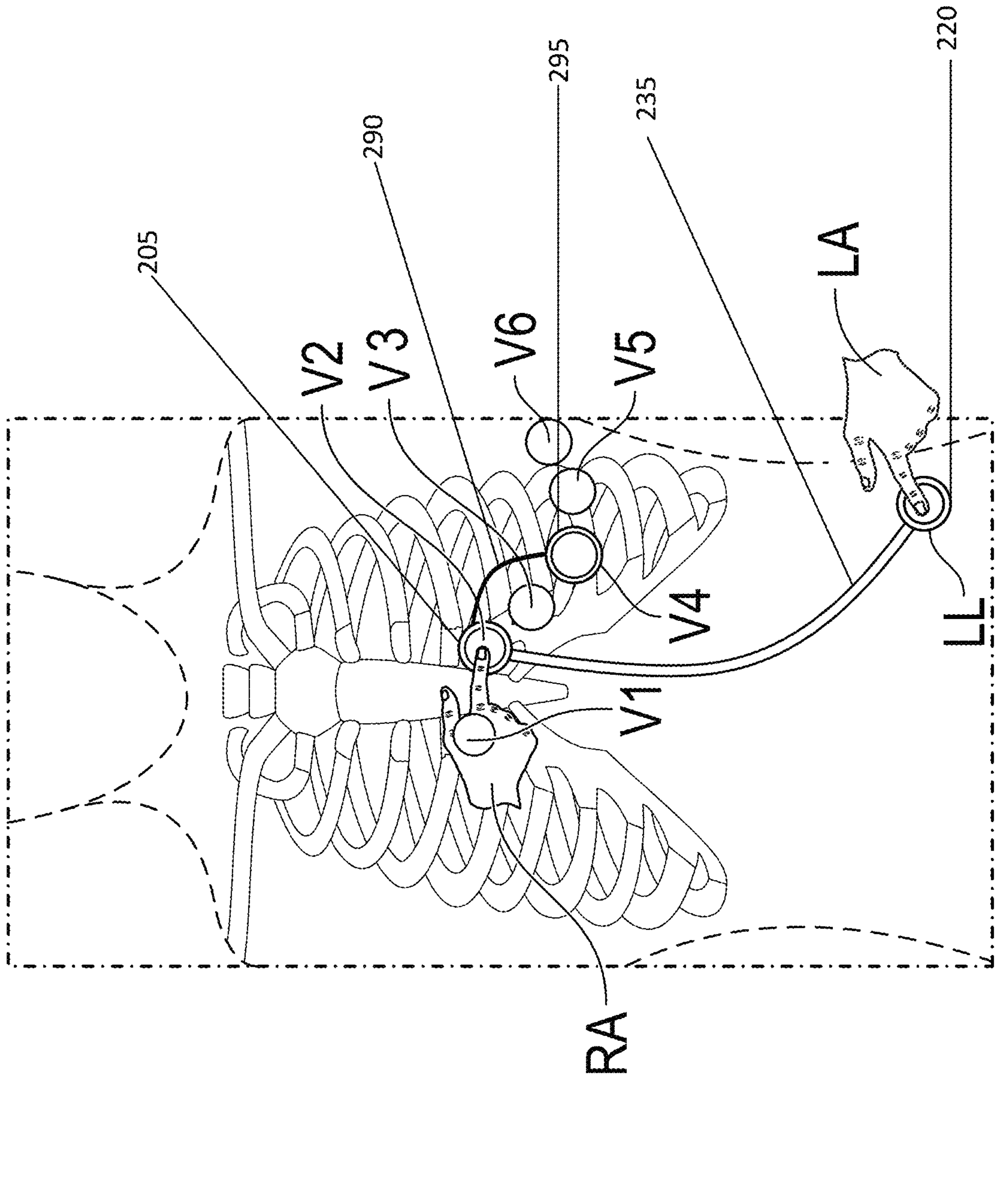
FIG. 3D illustrates the ECG monitoring device of FIG. 2A with an attachment for connecting to a third housing, in accordance with some embodiments of the present disclosure.

FIG. 3D illustrates an embodiment where the housing 205 may include an attachment 290, which may couple the housing 205 to a third housing 295. An electrode (not shown) may be positioned on an underside of the third housing 295 in such a way so as to make contact with the V4 position and thereby enable the ECG monitoring device 200 to take a four channel ECG. The attachment 290 may be an articulable arm, outrigger, or any other suitable articulable attachment that may couple the housing 295 to the housing 205, while keeping a vertical positioning of housing 205 and housing 295 consistent with each other. For example, upon a user pushing (e.g., exerting a force onto) housing 205 down on his/her chest in e.g., the V1 position, the attachment 290 may function to push (e.g., exert a similar force on) housing 295 down on the user's chest in the V4 position. The attachment 290 may be adjustable so that if the housing 205 is positioned to make contact with a different position on the user's chest, the housing 295 will still be positioned to make contact with the V4 position.

Figure 4A:
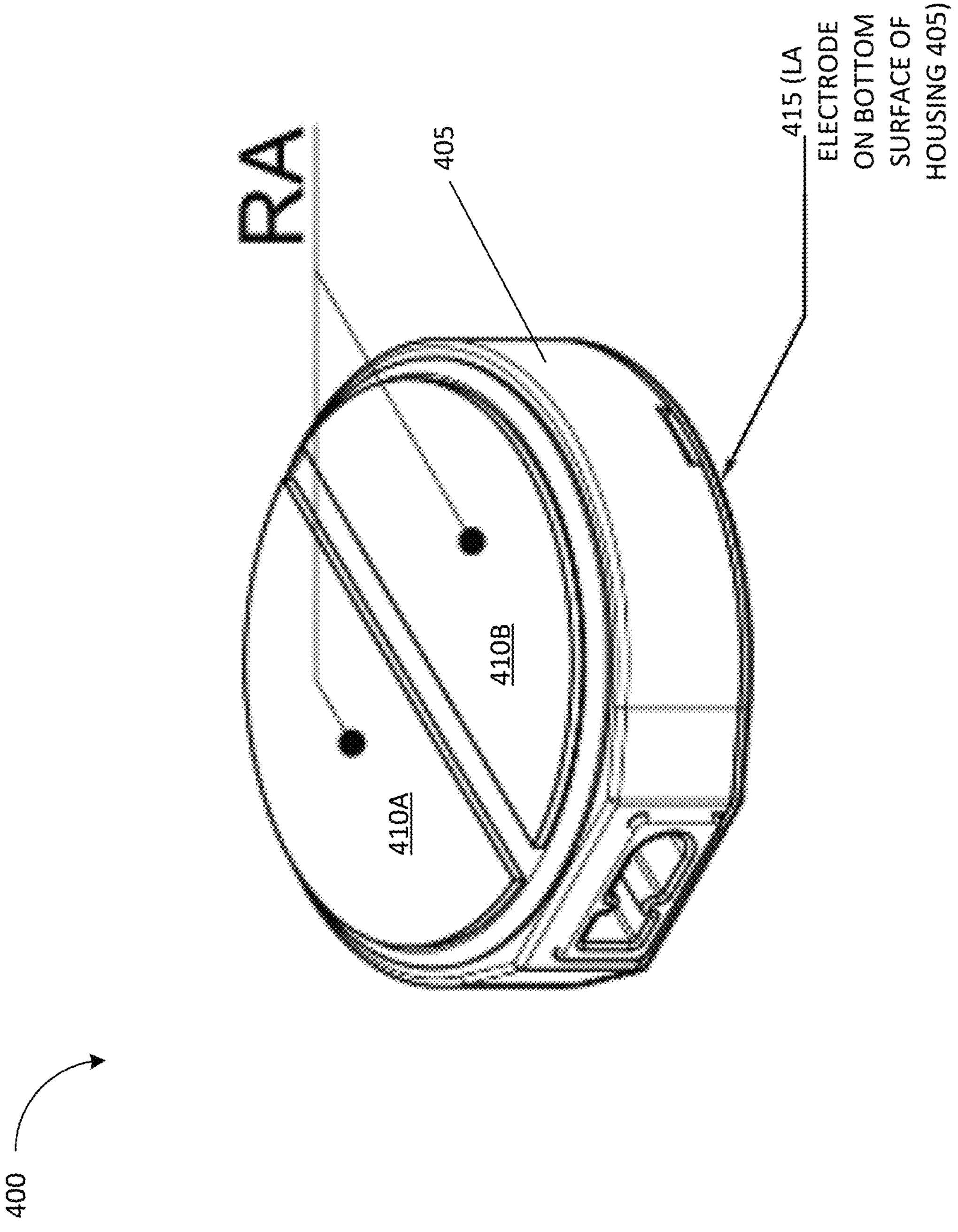
FIG. 4A is a diagram illustrating an ECG monitoring device, in accordance with some embodiments of the present disclosure.
Figure 4B:
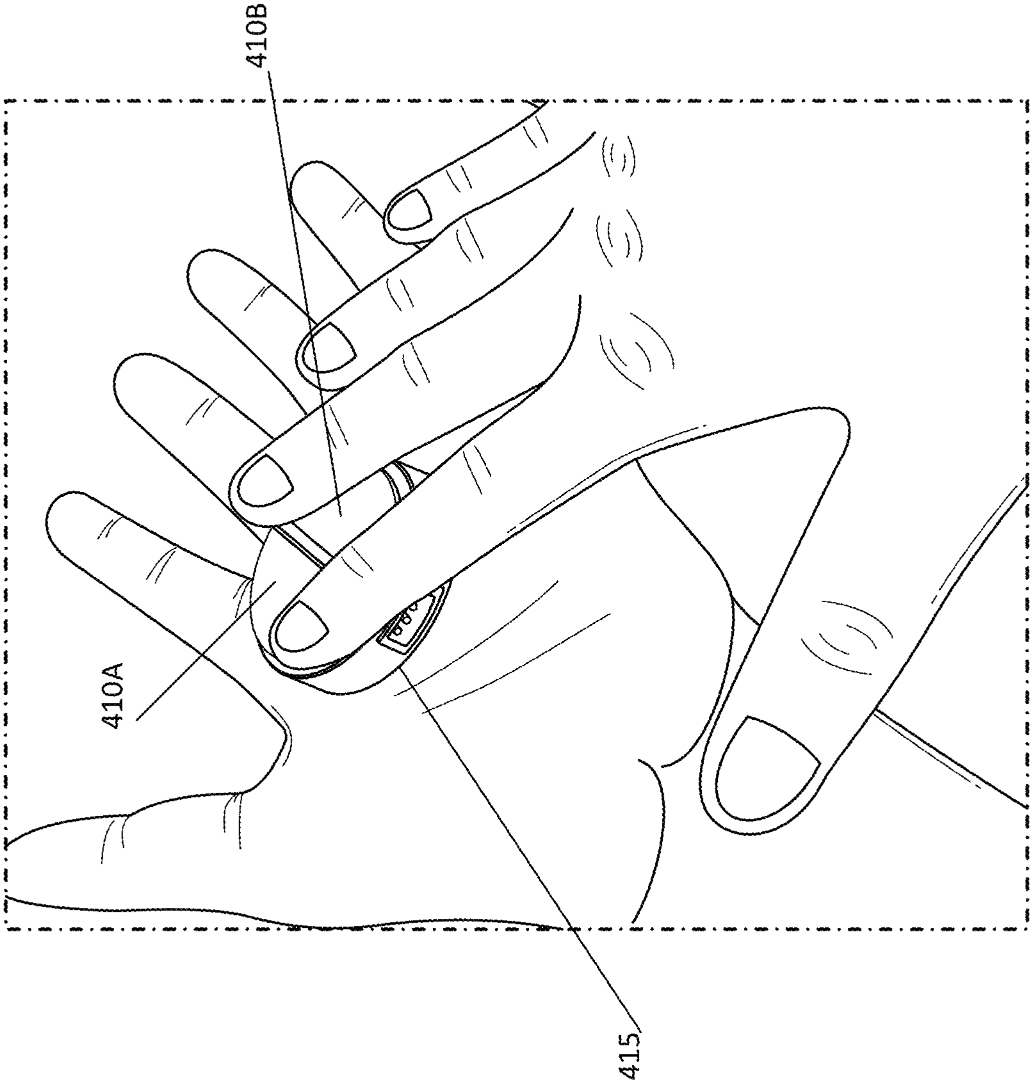
FIG. 4B illustrates the ECG monitoring device of FIG. 4A in operation, in accordance with some embodiments of the present disclosure.

FIG. 4A illustrates an ECG monitoring device 400 in accordance with some embodiments of the present disclosure. The ECG monitoring device 400 may comprise a single housing 405 upon which electrodes 410A and 410B may be mounted. The electrodes 410A and 410B may be mounted on a top surface of the housing 405. The ECG monitoring device 400 may further comprise an electrode 415 which may be mounted on a bottom surface of the housing 405. The housing 405 may include hardware as described herein with respect to FIG. 2B. In some embodiments, the electrodes 410A and 410B may correspond to RA electrodes and the electrode 415 may be a LA electrode. Thus, the user may contact the ECG monitoring device 400 as shown in FIG. 4B so as to take a single lead ECG. More specifically, the user may contact the ECG monitoring device 400 as shown in FIG. 4B, with the user's right arm (e.g., respective fingers of the user's right hand) contacting electrodes 410A and 410B while the user's left arm (left hand) is simultaneously contacting the electrode 415 so as to take a single lead (lead I) ECG. In some embodiments, ECG monitoring device 400 may be realized by disconnecting housing 205 from housing 220 (e.g., by removing cable 235 from housing 205) and utilizing housing 205 as a standalone device (or disconnecting housing 220 from housing 205 and utilizing housing 220 as a standalone device).

Figure 5A:
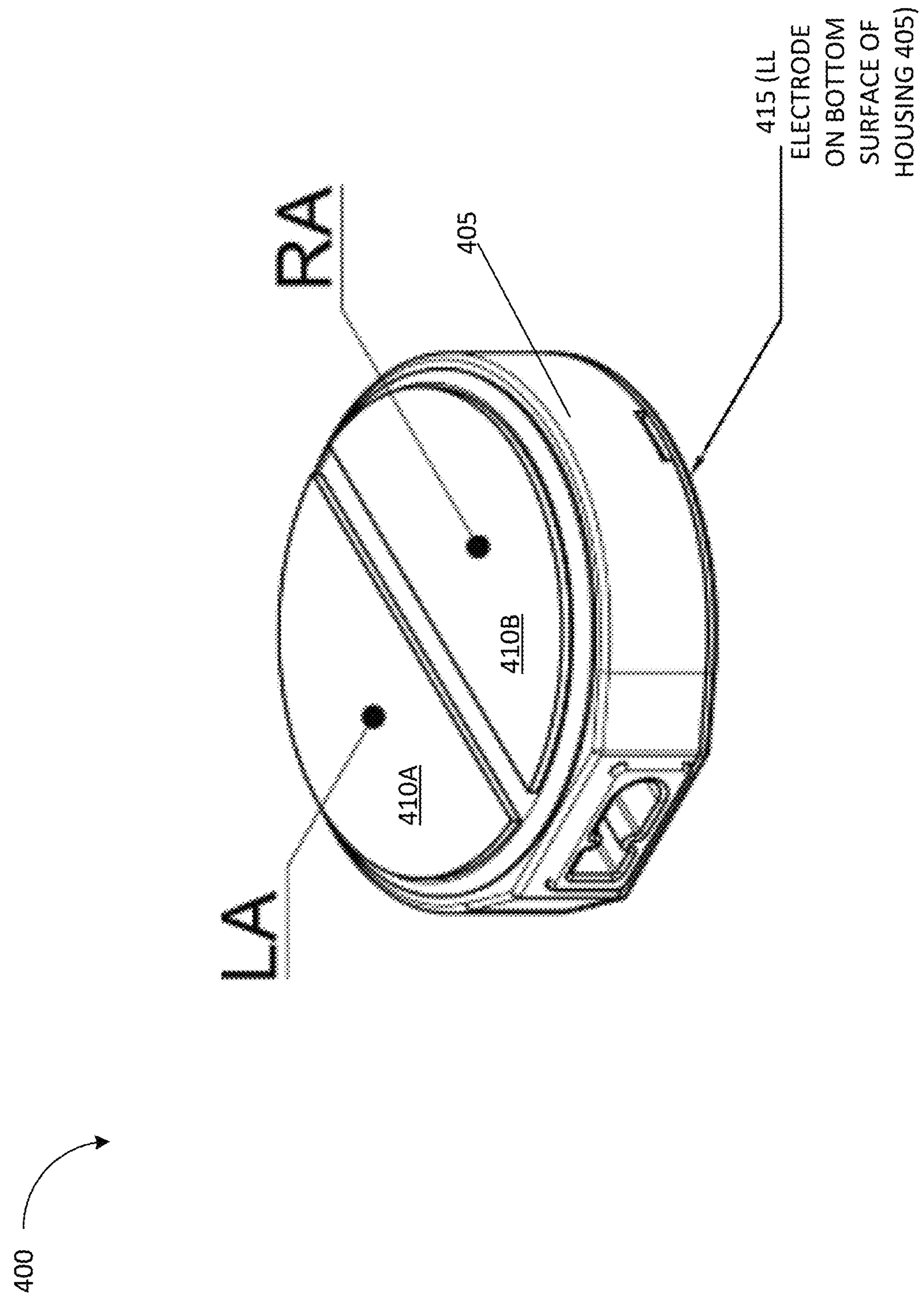
FIG. 5A is a diagram illustrating an ECG monitoring device, in accordance with some embodiments of the present disclosure.
Figure 5B:
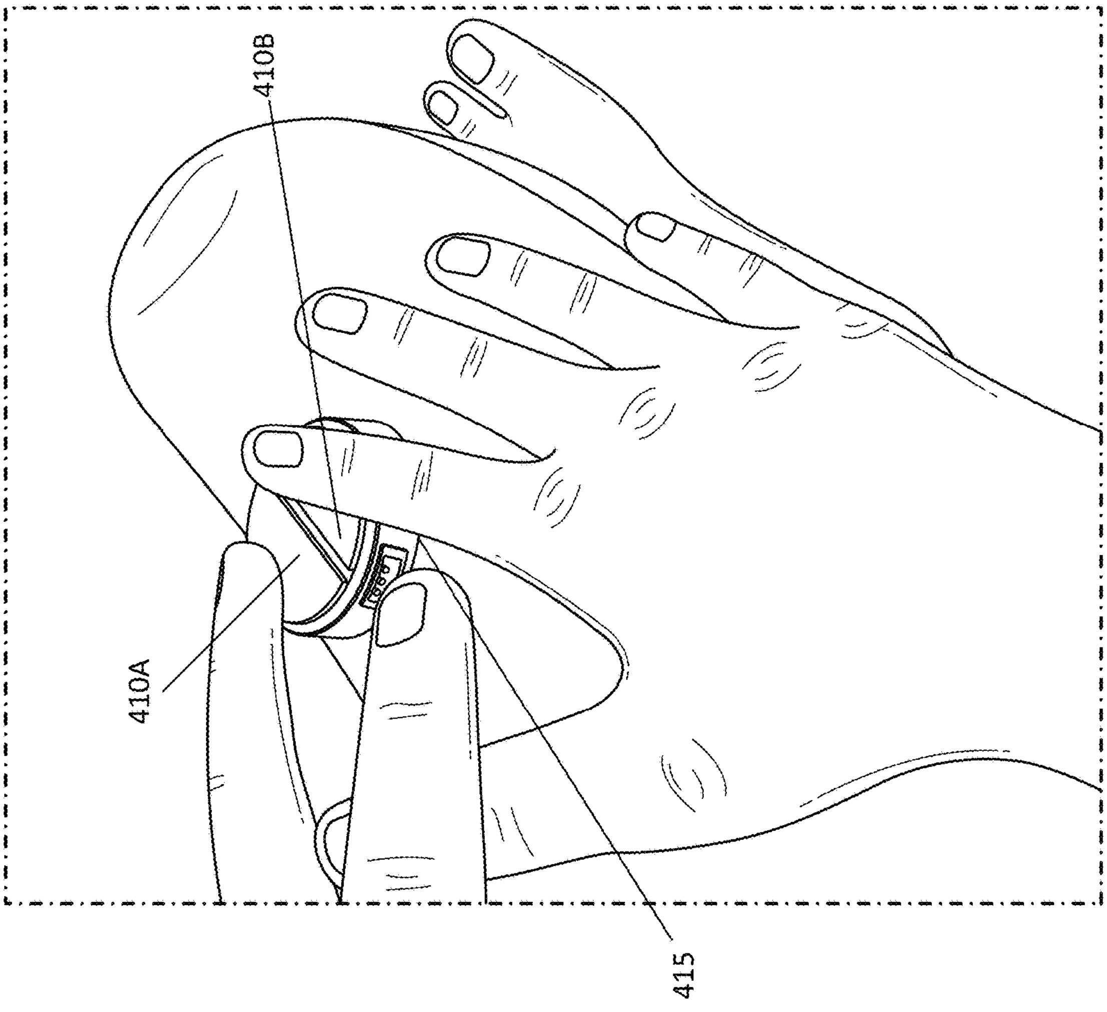
FIG. 5B illustrates the ECG monitoring device of FIG. 5A in operation, in accordance with some embodiments of the present disclosure.

FIG. 5A illustrates the ECG monitoring device 400 in accordance with another embodiment wherein the electrode 410A may correspond to an LA electrode, the electrode 410B may correspond to an RA electrode, and the electrode 415 may be an LL electrode. Thus, the user may contact the ECG monitoring device 400 as shown in FIG. 5B, with the user's right arm (right hand) contacting electrodes 410B, the user's left arm (left hand) contacting the electrode 410A, and the user's left leg contacting the electrode 415 so as to take a 2 lead (leads I and II) ECG.

Figure 6A:
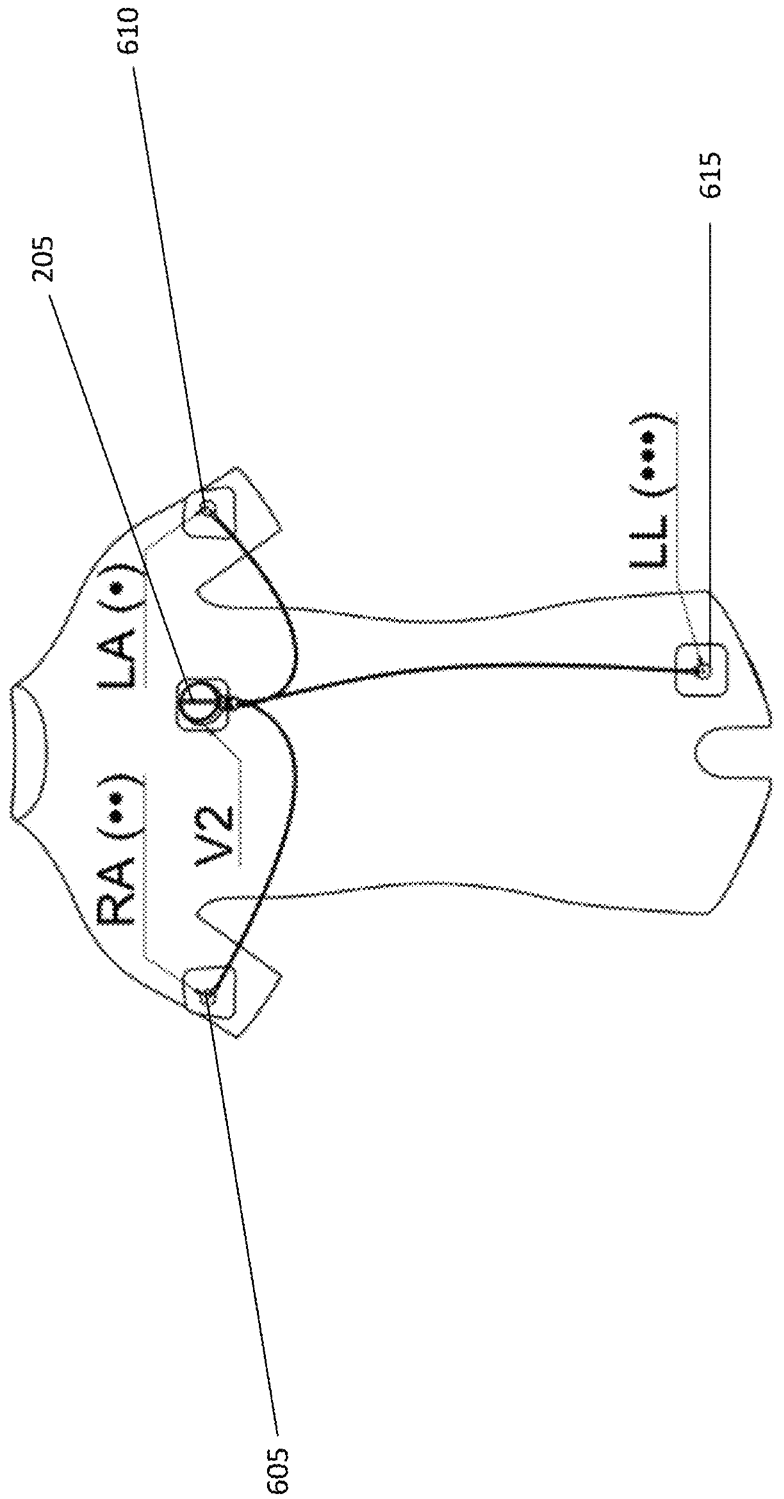
FIGS. 6A and 6B are diagrams illustrating an ECG monitoring device, in accordance with some embodiments of the present disclosure.

As discussed herein, the housing 205 may be disconnected from the housing 220 to operate as a standalone device. However, in some embodiments, a user may disconnect housing 220 from the housing 205 (e.g., by removing cable 235 from housing 220), and connect one or more adhesively attached electrodes as shown in FIG. 6A. FIG. 6A illustrates the housing 205 connected to electrodes 605, 610, and 615. Each of the electrodes 605, 610, and 615 may include an adhesive patch as is known in the art, which may allow them to stick to the body of the user in a desired location. Each of the electrodes 605, 610, and 615 may be connected via a dedicated cable to the connection socket 201 of the housing 205. In some embodiments where the housing 205 has multiple connection sockets, each of the electrodes 605, 610, and 615 may be connected via a dedicated cable to a respective connection socket. In addition, in some embodiments housing 205 itself may comprise an adhesive patch to enable it to be stuck to the body of the user without user intervention. The electrodes 605, 610, and 615 (as well as the electrode of housing 205) in the configuration shown in FIG. 6A may correspond to RA-V2-LA-LL electrodes and may record leads I, II, and V2 (in the example of FIG. 6A—although any V lead can be measured), while standard leads III, aVR, aVL, and aVF, are derived and leads V1, V3, V4, V5, and V6 are synthesized (assuming V2 was recorded). In another example, the electrode of housing 205 could be a V4 electrode and the electrodes 605, 610, and 615 (as well as the electrode of housing 205) may record leads I, II, and V4. In yet another example, a fifth electrode (not shown) could be attached (e.g., at the V4 position while the electrode of housing 205 is at the V2 position) thus providing an RA-V2-V4-LA-LL configuration for the electrodes which may measure leads I, II, V2, and V4.

Figure 6B:
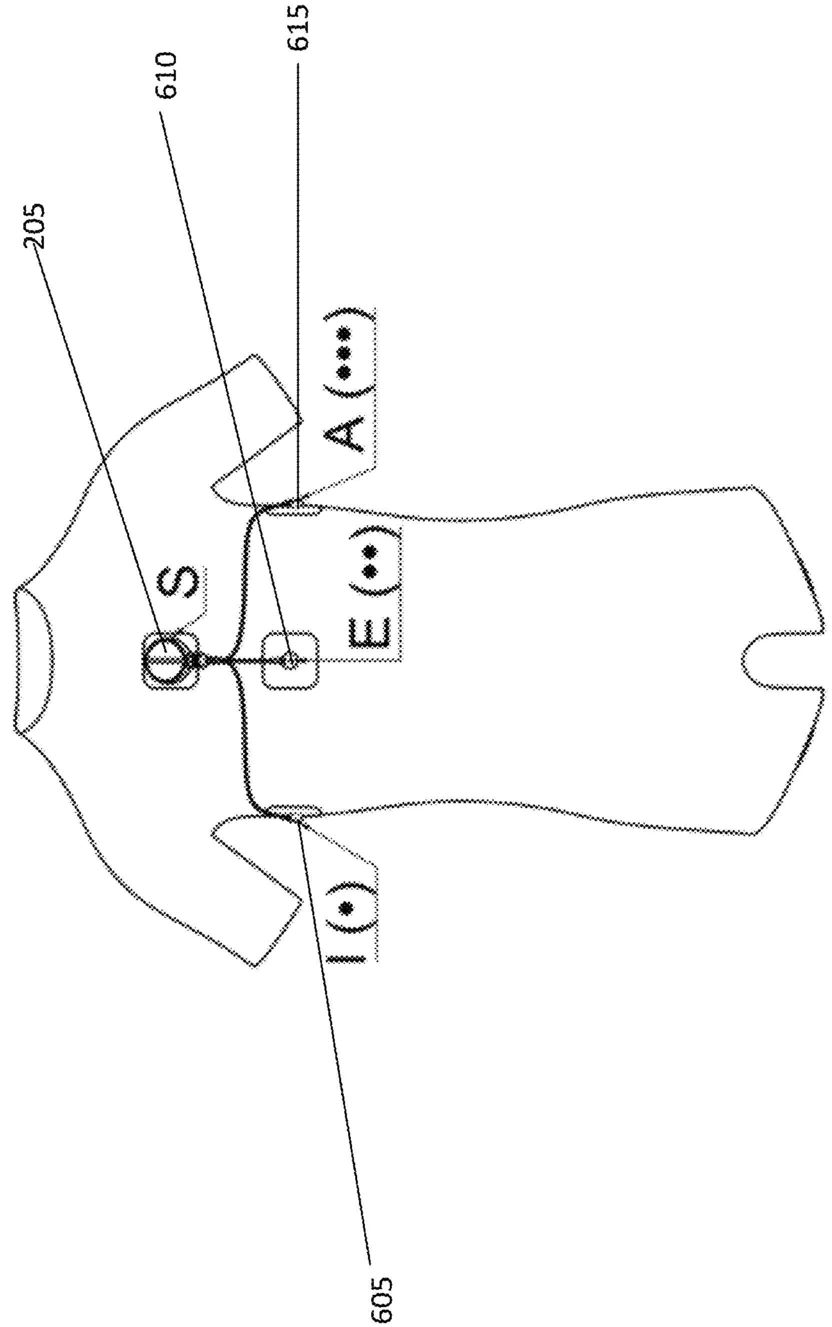

FIG. 6B illustrates the housing 205 connected to electrodes 605, 610, and 615 in an EASI configuration, where only five optimally placed electrodes (including ground) and only three signal channels are provided. The EASI configuration may provide a 12-lead ECG that is mathematically derived to resemble the conventionally recorded 12-lead ECG. The housing 205 may utilize the electrodes 605, 610, and 615 to record/measure ES, AS, and AI leads, and synthesize a 12 or 15 lead ECG.

ECG monitoring devices (e.g., ECG monitoring device 200) in accordance with embodiments of the present disclosure can acquire a standard 3-lead ECG using leads, I, II, and V2 (or any other V lead). Referring back to FIG. 2B, and as discussed herein, the processing device 206 may execute the module 207A in order to synthesize a full 12 lead set from the set of leads measured by the ECG monitoring device 200. The module 207A may comprise a lead conversion ML model which may function to synthesize the V1, V3, V4, V5, and V6 leads based on one or more of the measured/derived I, II, III, aVR, aVL, aVF, and V2 leads. In some embodiments, the lead conversion ML model may comprise a single dipole global model, that provides a "one size fits all" approach to lead conversion. A conversion model can be expressed mathematically as:

$$V\text{pred}=f(W,Vx)$$

Where Vpred are the predicted V leads, f( ) is a transfer function with input leads Vx (I, II, and V2 in this case), and coefficients (W). Appropriate coefficients W that will minimize the error between Vpred and actual sampled V lead signals (Vreal) (Min err=E|(Vreal−Vpred)|◯2) must be found.

Locating such appropriate coefficients W is a problem that may be solved using any appropriate method such as a supervised learning task or a curve fitting problem. In some embodiments, the module 207A may utilize linear optimization and the least square method (LS):

$$V\text{pred}=f(W,Vx)\rightarrow V\text{pred}=Vx\ W$$

By stacking many paired samples of Vx to form a matrix X and Y (given as Y=X.W), linear optimization and the LS method can be used to solve for W. More specifically, processing device 206 may prepare the matrix X and Y for Y=X.W, using the LS method to obtain a conversion coefficient:

$$X'=X\hat{}t$$

The covariance of X may then be given as:

$$\text{Cov}X=X'X$$

W may then be calculated as follows:

$$X\text{inv}=\text{inv}(\text{Cov}X)$$

$$W=\text{Cov}X\_\text{inv}*X'*Y,$$ (here we assume CovX is a full rank matrix).

Training data comprising e.g., 100,000 ECGs with average beats may be used for the training of the lead conversion ML model. The final conversion model is a matrix W having a 3 by 5 shape. The leads V1, V3, V4, V5, and V6 are predicted using the input leads I, II, V2.

In some embodiments, the processing device 206 may quantify the quality of the lead conversion ML model and determine whether a different lead conversion ML model (e.g., a more individualized model, or a multiple-dipole model) should be used. Techniques for quantifying the quality of a lead conversion ML model may be complicated since most statistical similarity methods are more closely related to amplitudes of every point, like the popular R-square method. However, the overall ECG morphology patterns which are used for interpretations are not based on amplitudes alone. For example, a Q wave is important for myocardial infarction detection, but its amplitude is generally much smaller than an R wave. One way to measure the quality of conversion is to compare the important ECG features used for ECG interpretations. Any appropriate algorithm (such as GE's EK12/12SL algorithm) can be used for this purpose. The data shown in table 1 below was obtained using the R-square ($R^2$) algorithm (shown directly below), however, any appropriate 12-lead measurement algorithm may be used.

TABLE 1

$$R^2 = \left\{1 - \frac{\sum[\text{Derived(sample k)} - \text{Measured(sample k)}]^2}{\sum[\text{Measured(sample k)}]^2}\right\}$$

| | V1 | V3 | V4 | V5 | V6 |
|---|---|---|---|---|---|
| $R^2$ (%) | 87 | 82 | 70 | 75 | 78 |

Figure 7A:
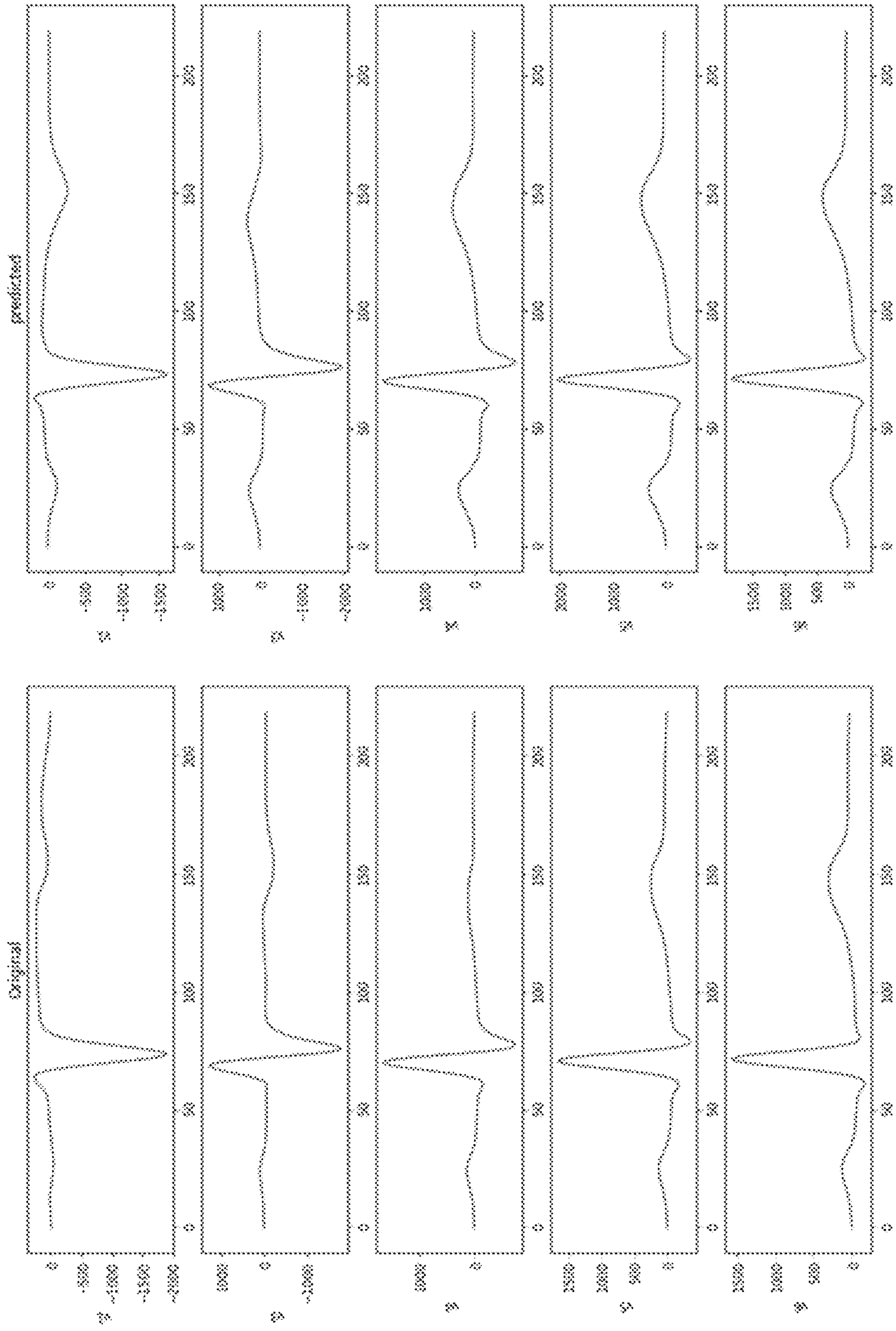
FIG. 7A illustrates a comparison of an ECG pattern of converted leads with an ECG pattern of measured leads, in accordance with some embodiments of the present disclosure.

As can be seen, R-V1 is higher than the other V leads. Theoretically, V1 is the most difficult to predict from leads I, II, V2, since it represents more right ventricular activity, while the input leads are more reflective of the left ventricular electric field. The V3 and V4 signals usually have higher amplitudes than other leads due to their proximity to the heart. FIG. 7A illustrates the results of lead conversion when the lead conversion ML model is a single dipole global model, with examples of the measured/original leads (left column) vs. converted/predicted leads (right column). As can be seen in FIG. 7A, the ECG pattern of converted leads accurately follows the ECG pattern for the measured/original leads.

Figure 7B:
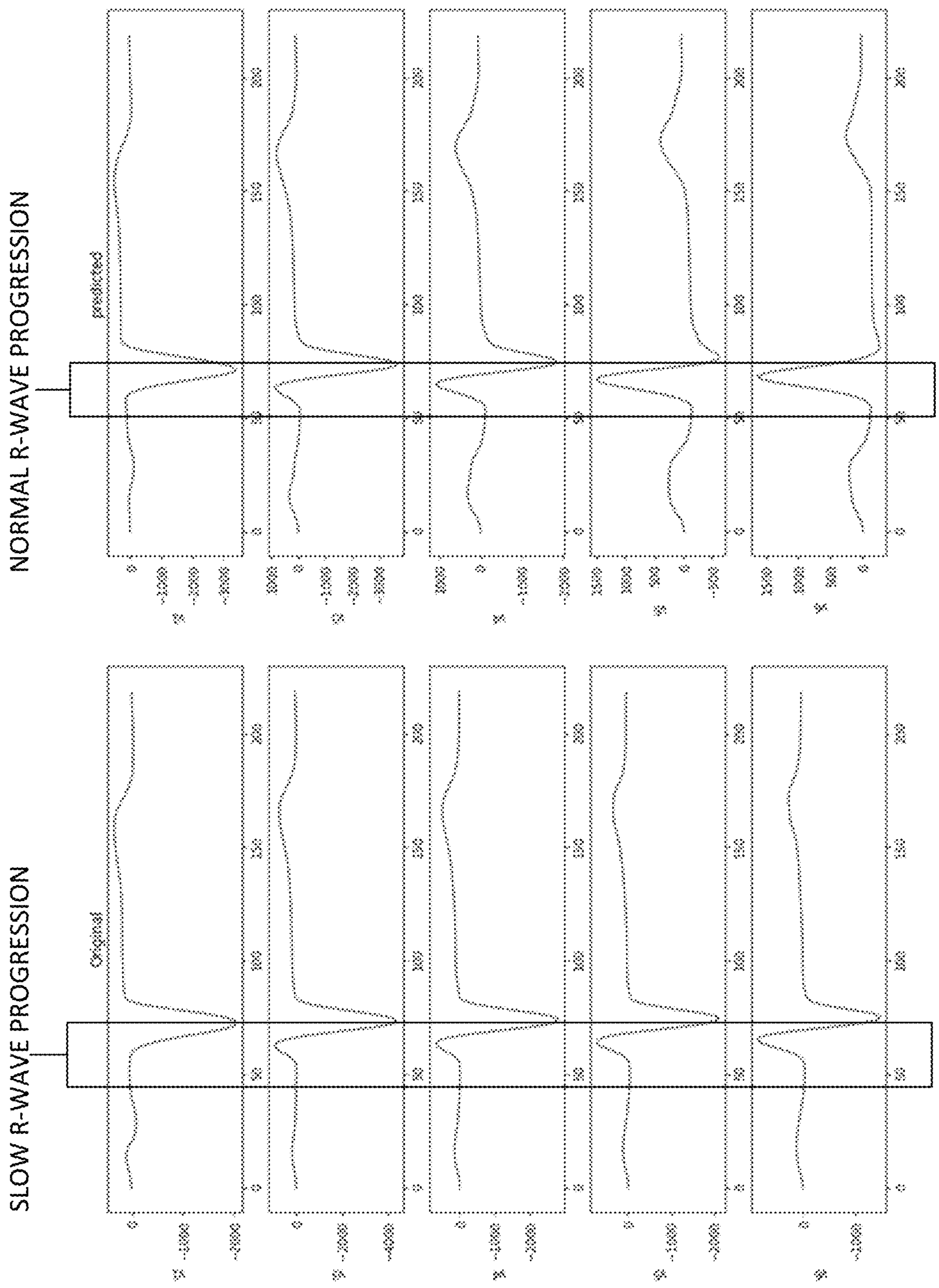
FIG. 7B illustrates a comparison of an ECG pattern of converted leads with an ECG pattern of measured leads with respect to an R-wave, in accordance with some embodiments of the present disclosure.

However, the processing device 206 may also determine that the performance provided by the single dipole global model is not sufficient. For example, FIG. 7B illustrates a pattern called 'slow R wave progression' in the measured/original leads (left column), which is a criterion for possible previous anterior infarction, while the converted/predicted leads (right column) have a 'normal' R wave progression from V3-V6. It may be difficult for an ML model that is trained with and follows a global trend of R wave progression of the majority of ECG samples, to avoid such issues. However, in such situations, the processing device 206 may alleviate this problem by selecting a different lead conversion ML model with a higher level of individualization or multiple dipoles.

A single pole cardiac source model may cover all phases of cardiac signal progression, including both atrial and ventricular depolarization and repolarization, while being relatively simple. However, such a model may be oversimplified in certain circumstances since a multiple-dipole model generally provides better accuracy than a single dipole model. Thus, in some embodiments, the processing device 206 may utilize a lead conversion ML model based on a multiple-dipole conversion model. The below table illustrates R-square statistics when a multiple-dipole model is used. As can be seen, both the QRS and ST-T segments show improved accuracy (relative to the single-dipole model in table 1 above), while the P-wave results are not improved. As a result, the lead conversion ML model used by processing device 206 may consider depolarization and repolarization separately.

TABLE 2

| | V1 | V3 | V4 | V5 | V6 |
|---|---|---|---|---|---|
| R^2 P (%) | 75 | 80 | 74 | 76 | 73 |
| R^2 QRS (%) | 88 | 84 | 74 | 78 | 78 |
| R^2 St-T (%) | 84 | 89 | 79 | 82 | 81 |

Referring to the basic optimization equation (Vpred=f(W, Vx)), it is clear that both a linear function f( ) and a non-linear function f( ) can be used for finding the W. In some embodiments, the processing device 206 may utilize a nonlinear lead conversion model in situations where the increased computational burden required for the use of a nonlinear model is justified by significantly superior performance.

A number of deep learning methods may also be used to synthesize a full 12 lead set from the set of leads measured by the ECG monitoring device 200. For example, the lead conversion ML model may utilize artificial neural networks (ANNs) for supervised classification, where the outcome of the model represents the probability of the input sample to be in a specific class of data or exhibits some peculiar characteristics. In another example, a data driven approach based on convolutional neural networks (CNNs) is used. By using convolution operations, the lead conversion ML model may take into account the correlation among temporally closed input samples to infer a single output data point. More specifically, a single output sample (each precordial lead) at a generic time t is affected by all the input samples (all limb leads) from $t-\tau$ to $t+\tau$. The value of $\tau$, which represents the receptive field of the network, highly depends on the model architecture and typically increases with its depth, i.e., the number of consecutive layers. The ability to generalize on unseen data, and avoid overfitting issues, is of primary importance for all data driven approaches. Complex models, along with small datasets, may lead to excellent performance on the training set, but may perform poorly on unseen data. Any appropriate regularization method may be used to optimize the model, such as inter and intra-layer normalization (e.g., batch normalization and layer normalization), and data augmentation techniques. Finally, to improve the effectiveness and efficiency of the model, the use of residual connections, i.e., an identity mapping that allow gradients to flow through a layer during the back-propagation of gradient-based optimization algorithms may be utilized.

The processing device 206 may execute module 207B in order to perform interpretation based on the synthesized full 12-lead set of ECG waveforms using an interpretation ML model. The module 207B may comprise an interpretation ML model which may function to determine (based on the full 12 lead set measured/generated by the processing device 206) interpretations indicating myocardial ischemia (anterior, lateral, ischemia), myocardial infarction (anterior, lateral mi), left and right bundle branch block and right ventricular hypertrophy, among others. The interpretation ML model may be trained to perform well on morphology-based abnormalities using the converted 12-leads. More specifically, the interpretation ML model may comprise a deep neural network (DNN) model that is trained with converted lead signals, so that it can identify new ECG feature patterns, even if they are not identical with the original ones, thus enabling the interpretation ML model to differentiate among different abnormalities. The interpretation ML model may be a convolutional DNN with 6 residual blocks and 3 fully connected layers. The ML interpretation model may also have dropout and batch normalization layers to improve the generalization.

The interpretation ML model may be trained using a 12-lead ECG database (not shown), which has ECG data for a large number of 12-lead ECGs, each with e.g., 10 seconds of data. The 12-lead ECG database may include ECG data with various types of ECG abnormalities. In the training data, morphology-based ECGs may be clustered into 6 categories: ischemia, infarction, left bundle branch block (LBBB), right bundle branch block (RBBB), left ventricle hypertrophy (LVH), and others. Of those ECGs, a majority may be used for training, while the remainder are used for testing. Experimental data has shown that training the interpretation ML model on a converted lead set optimizes the interpretation performance. Thus, in some embodiments the interpretation ML model may be further trained on a converted lead set to optimize its interpretation performance. More specifically, the interpretation ML model is first trained and tested with the originally sampled 12-lead data and the interpretation performance is recorded. The interpretation ML model is then reinitialized and retrained/retested with converted 12-lead data, and the interpretation performance is recorded.

Figure 8:
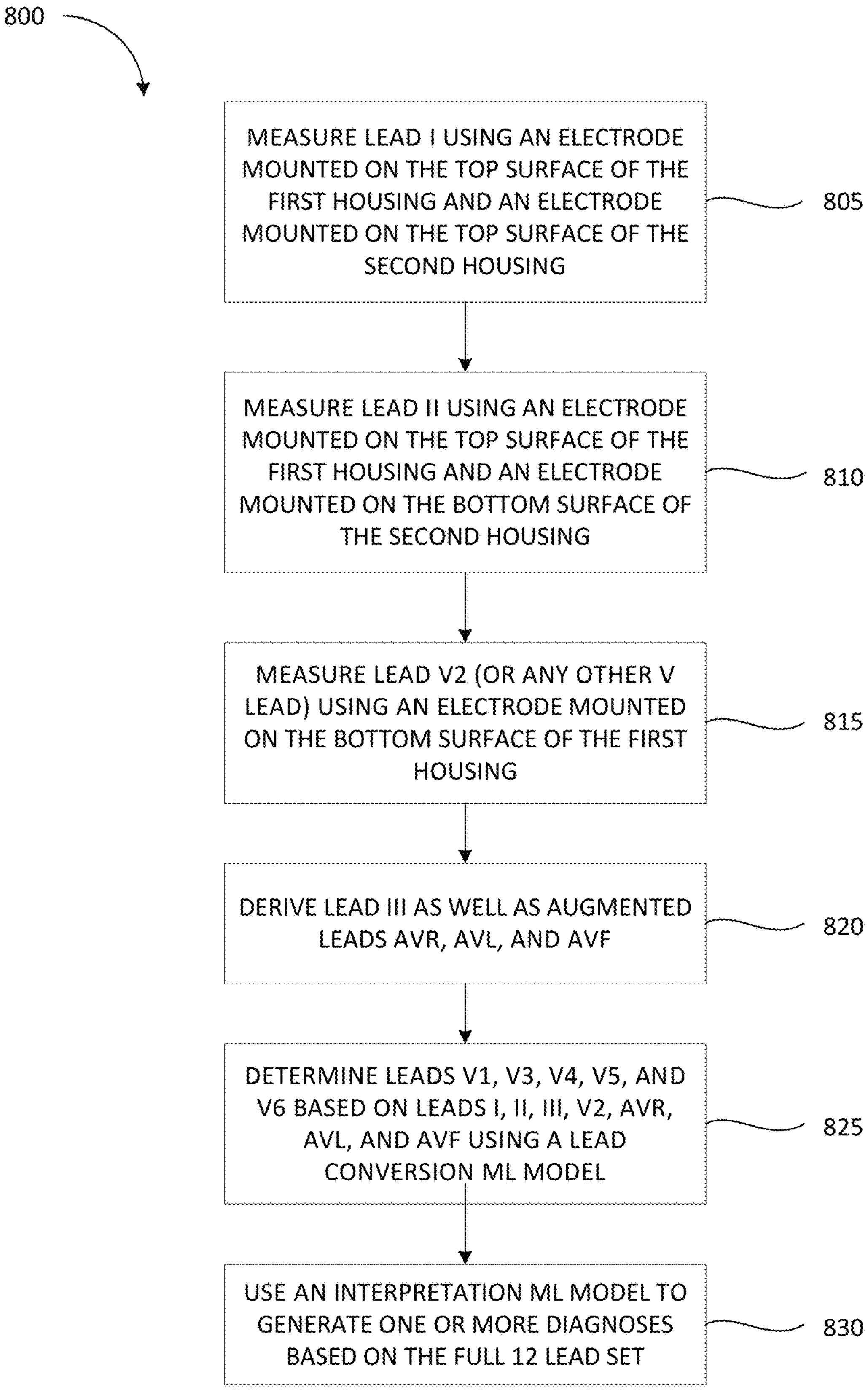
FIG. 8 is a flow diagram of a method for performing a twelve-lead ECG with a small form factor three-electrode device, in accordance with some embodiments of the present disclosure.

FIG. 8 is a flow diagram of a method 800 for performing a twelve-lead ECG with a small form factor three-electrode device, in accordance with some embodiments of the present disclosure. Method 800 may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. In some embodiments, the method 800 may be performed by the ECG monitoring device 200 (e.g., via processing device 206) illustrated in FIG. 2A.

Referring to FIGS. 2A and 2B as well, at block 805, processing device 206 may measure Lead I from a first electrical signal of a first electrode and a second electrical signal of a second electrode. More specifically, lead I may be measured using electrode 210 mounted on the top surface of the first housing 205 and electrode 225 mounted on the top surface of the second housing 220. At block 810, processing device 206 may measure Lead II from the second electrical signal and a third electrical signal from a third electrode. More specifically, lead II may be measured using electrode 210 mounted on the top surface of the first housing 205 and electrode 230 mounted on the bottom surface of the second housing 220.

At block 815, processing device 206 may measure lead V2 (or any other V lead using electrode 215 mounted on the bottom surface of the first housing 205 once it comes into contact with the user. In some embodiments, leads I, II, and V2 are measured concurrently (e.g., the user places electrodes for leads I, II, and V2 and obtains all measurements contemporaneously, concurrently, or substantially simultaneously). At block 820, processing device 206 may derive lead III as well as augmented leads aVR, aVL, and aVF. As discussed above, the augmented vector right (aVR) lead is equal to RA−(LA+LL)/2 or −(I+II)/2, the augmented vector left (aVL) lead is equal to LA−(RA+LL)/2 or I−II/2, and the augmented vector foot (aVF) lead is equal to LL−(RA+LA)/2 or II−I/2.

At block 825, processing device 206 may determine leads V1, V3, V4, V5, and V6 based on leads I, II, III, V2, aVR, aVL, and aVF using a lead conversion ML model (e.g., by executing module 207A) as discussed herein. At block 830, the processing device 206 may use an interpretation ML model (e.g., by executing module 207B) to generate one or more interpretations (diagnoses) based on the full 12 lead set.

In one embodiment, the interpretation ML model is built based on a deep convolution structure. The input layer handles multi-leads ECG as a spatial image with one dimension for time axis, and another dimension for multiple channels. The ECG channels can have regular order of lead I, II, III, AVR, AVL, AVF, V1-V6. Alternatively, it may have a more physiological meaningful order, called 'Cabrera format', in which the frontal plane leads are in the order of lead aVL, I, aVR, II, aVF, III, and V1-V6. In another input format, only Cabrera format limb leads and one actual measured precordial lead are used to form input ECG image.

A 2-D convolution layer may be used to process the input ECG image, instead of 1-D convolution model as used by most other ECG training models. The training model may include 4-10 blocks of convolution/residual layers, followed by 2-4 fully connected layers. The output layer is a multiple classification layer with possible more than one class is identified, like 'Myocardial infarction' and 'Left Ventricle Hypertrophy', or 'Right bundle branch block' and 'Inferior Ischemia'.

In some embodiments, the interpretation ML model is trained with a large labeled training set with many epochs. To prevent overfitting and improve generalization, random connection drop and batch normalization may be used. Data are divided into training, validation, and test sets. The validation set is used to prevent overfitting and training during the training process. The test set is used for final performance check. The data sets are formed with existing 12-lead diagnostic ECG database first. And the second data sets will be formed with actual sampled ECG from targeted device described here. A transfer learning can be used to only adjust few layers of the deep-learning model for the $2^{nd}$ data set.

The comparisons and analysis described herein can be used to draw conclusions and insights into the patient's health status (generate interpretations), which includes potential health issues that the patient may be experiencing at the time of measurement or at future times. Conclusions and determinations may be predictive of future health conditions or diagnostic of conditions that the patient already has. The conclusions and determinations may also include insights into the effectiveness or risks associated with drugs or medications that the patient may be taking, have taken or may be contemplating taking in the future. In addition, the comparisons and analysis can be used to determine behaviors and activities that may reduce or increase risk of an adverse event. Based on the comparisons and analysis described herein, the ECG data can be classified according to a level of risk of being an adverse event. For example, the ECG data can be classified as normal, low risk, moderate risk, high risk, and/or abnormal. The normal and abnormal designation may require health care professional evaluation, diagnosis, and/or confirmation.

Diagnosis and determination of an abnormality, an adverse event, or a disease state by an ECG monitoring device in accordance with embodiments of the present disclosure may be reviewed by physicians and other health care professionals and can be transmitted to the servers and database to be tagged with and associated with the corresponding ECG data. The diagnosis and determination may be based on analysis of ECG data or may be determined using other tests or examination procedures. Professional diagnosis and determinations can be extracted from the patient's electronic health records, can be entered into the system by the patient, or can be entered into the system by the medical professional. The conclusions and determinations of the system can be compared with actual diagnosis and determinations from medical professions to validate and/or refine the machine learning algorithms used by the system. The time of occurrence and duration of the abnormality, adverse event or disease state can also be included in the database, such that the ECG data corresponding with the occurrence and/or the ECG data preceding and/or following the abnormality, adverse event or disease state can be associated together and analyzed. The length of time preceding or following the abnormality may be predetermined and be up to 1 to 30 days, or greater than 1 to 12 months. Analysis of the time before the abnormality, adverse event or disease state may allow the system to identify patterns or correlations of various ECG features that precede the occurrence of the abnormality, adverse event or disease state, thereby providing advance detection or warning of the abnormality, adverse event or disease state. Analysis of the time following the abnormality, adverse event or disease state can provide information regarding the efficacy of treatments and/or provide the patient or physician information regarding disease progression, such as whether the patient's condition in improving, worsening or staying the same. The diagnosis and determination can also be used for indexing by, for example, including it in the metadata associated with the corresponding ECG data.

As described herein, various parameters may be included in the database along with the ECG data. These may include the patient's age, gender, weight, blood pressure, medications, behaviors, habits, activities, food consumption, drink consumption, drugs, medical history and other factors that may influence a patient's ECG signal. The additional parameters may or may not be used in the comparison of the changes in ECG signal over time and circumstances.

The conclusions, determinations, and/or insights into the patient's health generated by the system may be communicated to the patient directly or via the patient's caregiver (doctor or other healthcare professional). For example, the patient can be sent an email or text message that is automatically generated by the system. The email or text message can be a notification which directs the patient to log onto a secure site to retrieve the full conclusion, determination or insight, or the email or text message can include the conclusion, determination or insight. Alternatively, or additionally, the email or text message can be sent to the patient's caregiver. The notification may also be provided via an application on a smartphone, tablet, laptop, desktop or other computing device.

The ECG data and the associated metadata and other related data as described herein can be stored in a central database, a cloud database, or a combination of the two. The data can be indexed, searched, and/or sorted according to any of the features, parameters, or criteria described herein. The system can analyze the ECG data of a single patient, and it can also analyze the ECG data of a group of patients, which can be selected according to any of the features, parameters or criteria described herein. When analyzing data from a single patient, it may be desirable to reduce and/or correct for the intra-individual variability of the ECG data, so that comparison of one set of ECG data taken at one particular time with another set of ECG data taken at another time reveals differences resulting from changes in health status and not from changes in the type of ECG recording device used, changes in lead and electrode placement, changes in the condition of the skin (i.e. dry, sweaty, conductive gel applied or not applied), and the like. As described above, consistent lead and electrode placement can help reduce variability in the ECG readings. The system can also retrieve the patient's ECG data that were taken under similar circumstances and can analyze this subset of ECG data.

Figure 9:
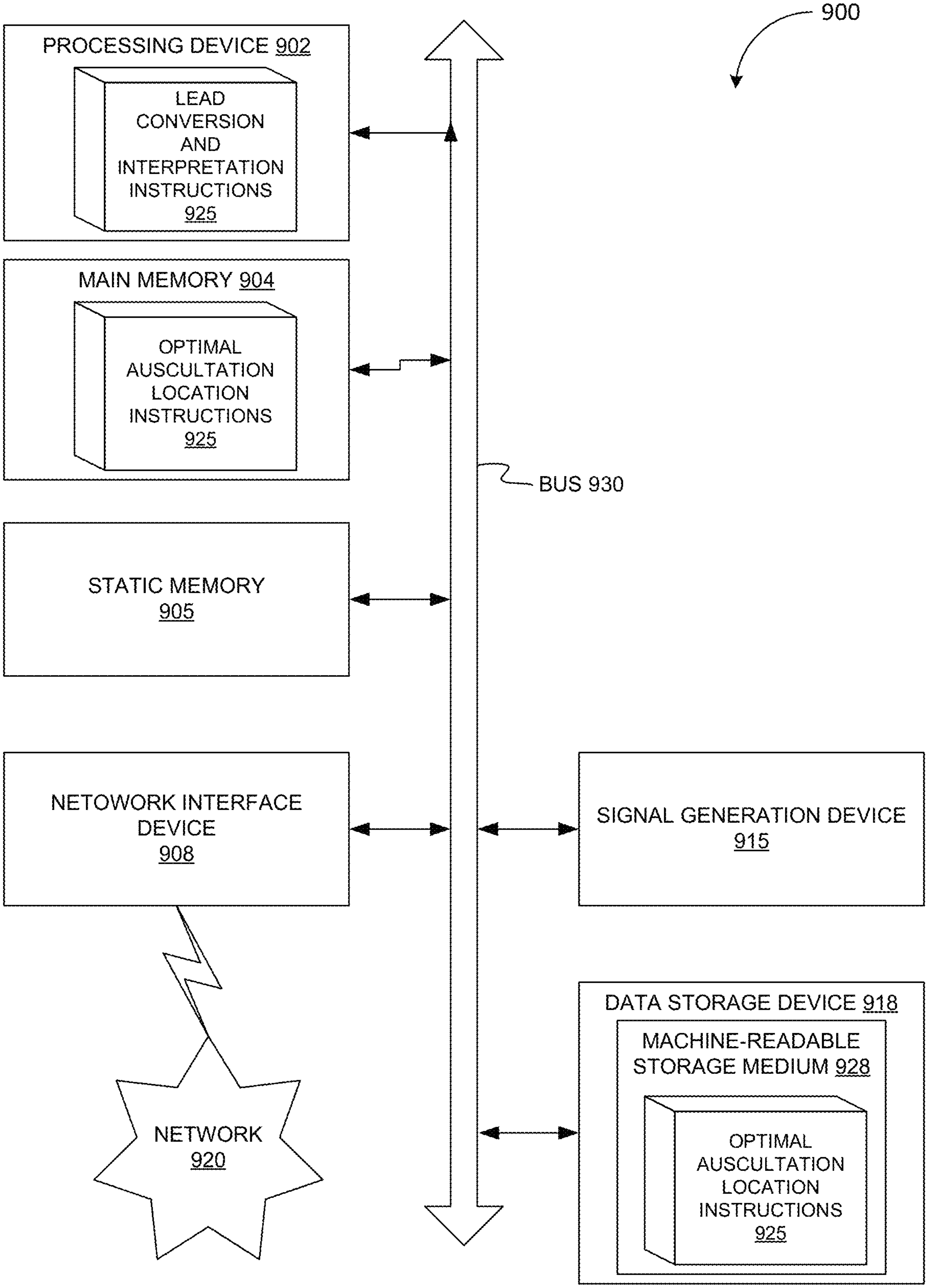
FIG. 9 is a block diagram of an example computing device that may perform one or more of the operations described herein, in accordance with some embodiments of the present disclosure.

FIG. 9 illustrates a diagrammatic representation of a machine in the example form of a computer system 900 within which a set of instructions, for causing the machine to perform any one or more of the methodologies discussed herein. In alternative embodiments, the machine may be connected (e.g., networked) to other machines in a local area network (LAN), an intranet, an extranet, or the Internet. Further, while only a single machine is illustrated, the term "machine" shall also be taken to include any collection of machines that individually or jointly execute a set (or multiple sets) of instructions to perform any one or more of the methodologies discussed herein.

The exemplary computer system 900 includes a processing device 902, a main memory 904 (e.g., read-only memory (ROM), flash memory, dynamic random access memory (DRAM), a static memory 906 (e.g., flash memory, static random access memory (SRAM), etc.), and a data storage device 918, which communicate with each other via a bus 930. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Computing device 900 may further include a network interface device 908 which may communicate with a network 920. Processing device 902 represents one or more general-purpose processing devices such as a microprocessor, central processing unit, or the like. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device 902 may also be one or more special-purpose processing devices such as an application specific integrated circuit (ASIC), a field programmable gate array (FPGA), a digital signal processor (DSP), network processor, or the like. The processing device 902 is configured to execute lead synthesis and interpretation generation instructions 925, for performing the operations and steps discussed herein.

The data storage device 915 may include a machine-readable storage medium 928, on which is stored one or more sets of lead synthesis and interpretation generation instructions 925 (e.g., software) embodying any one or more of the methodologies of functions described herein. The lead synthesis and interpretation generation instructions 925 may also reside, completely or at least partially, within the main memory 904 or within the processing device 902 during execution thereof by the computer system 900; the main memory 904 and the processing device 902 also constituting machine-readable storage media. The lead synthesis and interpretation generation instructions 925 may further be transmitted or received over a network 920 via the network interface device 908.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus comprising:

a first housing comprising:

a first set of electrodes to contact a first location and second location of a user; and a cable; and a second housing having a circular shape, the second housing operatively coupled to the first housing via the cable, wherein the second housing comprises a socket in which the cable is removably attached, the second housing further comprising:

a second set of electrodes to contact a third location and a fourth location of the user;

a memory; and a processing device operatively coupled to the second set of electrodes and the memory, the processing device configured to:

derive a predetermined set of electrocardiogram (ECG) waveforms of the user by:

measuring, using the first set of electrodes and the second set of electrodes, a first set of ECG waveforms of the user, the first set of ECG waveforms corresponding to ECG lead waveforms formed by the first and second set of electrodes; and synthesizing, using a machine learning (ML) model, a second set of ECG waveforms of the user based on the measured first set of ECG waveforms, the second set of ECG waveforms including any ECG lead waveforms not formed by the first set of electrodes and the second set of electrodes together, wherein the ML model is a multiple-dipole conversion model that considers cardiac depolarization and repolarization separately.

2. The apparatus of claim 1, wherein:

one or more of the first set of electrodes are positioned on a top side of the first housing to contact the first location of the user and one or more of the first set of electrodes are positioned on a bottom side of the first housing to contact the second location of the user; and one or more of the second set of electrodes are positioned on a top side of the second housing to contact the third location of the user and one or more of the second set of electrodes are positioned on a bottom side of the second housing to contact the fourth location of the user.

3. The apparatus of claim 1, wherein the processing device is further configured to:

determine one or more diagnoses based on the first and second set of ECG waveforms.

4. The apparatus of claim 3, wherein the second housing further comprises:

a transceiver to transmit the one or more diagnoses to a computing device.

5. The apparatus of claim 1, wherein the one or more of the first set of electrodes positioned on the top side of the first housing comprises a single electrode to contact the first location of the user, wherein the first location of the user corresponds to a left arm of the user.

6. The apparatus of claim 1, wherein the one or more of the first set of electrodes positioned on the top side of the first housing comprises a first electrode and a second electrode positioned on the top side of the first housing to contact the first location of the user, wherein the first location of the user corresponds to a left arm of the user.

7. The apparatus of claim 1, wherein the first, second, third, and fourth locations of the user correspond to a right arm, chest, left arm, and left leg of the user respectively.

8. The apparatus of claim 1, wherein each of the first set of electrodes and each of the second set of electrodes comprises an adhesive material to maintain contact between the electrode and a respective location of the user.

9. An apparatus comprising:
- a housing having a circular shape, the housing comprising:
  - a set of electrodes to contact two or more locations of a user;
  - a socket configured to removably couple to a cable;
  - a memory; and
  - a processing device operatively coupled to the set of electrodes, the socket, and the memory, the processing device configured to:
    - derive a predetermined set of electrocardiogram (ECG) waveforms of the user by:
      - measuring, using the set of electrodes, a first set of ECG waveforms of the user, the first set of ECG waveforms corresponding to ECG lead waveforms formed by the set of electrodes; and
      - synthesizing, using a machine learning (ML) model, a second set of ECG waveforms of the user based on the measured first set of ECG waveforms, the second set of ECG waveforms including any ECG lead waveforms not formed by the set of electrodes, wherein the ML model is a multiple-dipole conversion model that considers cardiac depolarization and repolarization separately.

10. The apparatus of claim 9, wherein the set of electrodes comprises:
- a first electrode and a second electrode positioned on a top side of the housing to contact the first and the second location of the user respectively; and
- a third electrode are positioned on a bottom side of the housing to contact a third location of the user, wherein the processing device performs a two-lead ECG.

11. The apparatus of claim 9, wherein the set of electrodes comprises:
- a first electrode positioned on a top side of the housing to contact the first location of the user; and
- a second electrode positioned on a bottom side of the housing to contact the second location of the user, wherein the processing device performs a single-lead ECG.

12. The apparatus of claim 9, wherein the processing device is further configured to:
- determine one or more diagnoses based on the first and second set of ECG waveforms.

13. The apparatus of claim 12, wherein the housing further comprises:
- a transceiver to transmit the one or more diagnoses to a computing device.

14. The apparatus of claim 9, wherein each of the set of electrodes comprises an adhesive material to maintain contact between the electrode and a respective location of the user.

15. A system comprising:
- an electrocardiogram (ECG) monitoring device comprising:
  - a first housing comprising a first set of electrodes to contact a first location and second location of a user;
  - a cable; and
  - a second housing having a circular shape, the second housing operatively coupled to the first housing via the cable, wherein the second housing comprises a socket in which the cable is removably attached, the second housing further comprising:
    - a second set of electrodes to contact a third location and a fourth location of the user;
    - a memory; and
    - a processing device operatively coupled to the second set of electrodes and the memory, the processing device configured to:
      - derive a predetermined set of electrocardiogram (ECG) waveforms of the user by:
        - measuring, using the first set of electrodes and the second set of electrodes, a first set of ECG waveforms of the user, the first set of ECG waveforms corresponding to ECG lead waveforms formed by the first and second set of electrodes; and
        - synthesizing, using a machine learning (ML) model, a second set of ECG waveforms of the user based on the measured first set of ECG waveforms, the second set of ECG waveforms including any ECG lead waveforms not formed by the first set of electrodes and the second set of electrodes together, wherein the ML model is a multiple-dipole conversion model that considers cardiac depolarization and repolarization separately; and
      - determine one or more diagnoses based on the predetermined set of ECG waveforms; and
- a computing device to:
  - provide instructions to the user for placing the ECG monitoring device on a body of the user such that each of the set of electrodes is contacting a respective location of the user; and
  - receive the determined one or more diagnoses from the ECG monitoring device.

16. The system of claim 15, wherein the second housing further comprises:
- a transceiver to transmit the one or more diagnoses to the computing device.

17. The system of claim 15, wherein the computing device further comprises:
- a display to display the determined one or more diagnoses.

18. The system of claim 15, wherein:
- one or more of the first set of electrodes are positioned on a top side of the first housing to contact the first location of the user and one or more of the first set of electrodes are positioned on a bottom side of the first housing to contact the second location of the user; and
- one or more of the second set of electrodes are positioned on a top side of the second housing to contact the third location of the user and one or more of the second set of electrodes are positioned on a bottom side of the second housing to contact the fourth location of the user.

19. The system of claim 15, wherein the first, second, third, and fourth locations of the user correspond to a right arm, chest, left arm, and left leg of the user respectively.

* * * * *